United States Patent [19]

Bridges

[11] Patent Number: 5,704,355
[45] Date of Patent: Jan. 6, 1998

[54] NON-INVASIVE SYSTEM FOR BREAST CANCER DETECTION

[76] Inventor: Jack E. Bridges, 1937 Fenton La., Park Ridge, Ill. 60068

[21] Appl. No.: 492,998

[22] Filed: Jun. 21, 1995

Related U.S. Application Data

[63] Continuation-in-part of Ser. No. 269,691, Jul. 1, 1994, abandoned.

[51] Int. Cl.$^6$ ........................................................ A61B 5/05
[52] U.S. Cl. ........................ 128/653.1; 607/101; 607/154
[58] Field of Search .............................. 128/653.1, 633, 128/664, 665, 660.01, 660.02, 660.06, 915; 364/413.25; 600/2; 606/2, 12, 33; 250/330–334, 358.1, 363.01; 607/100, 101, 97, 154

[56] References Cited

U.S. PATENT DOCUMENTS

| | | |
|---|---|---|
| 4,307,726 | 12/1981 | Paulson et al. . |
| 4,407,292 | 10/1983 | Edrich . |
| 4,641,659 | 2/1987 | Sepponen ........................ 128/653.1 |
| 4,767,717 | 8/1988 | Baisden . |
| 4,774,961 | 10/1988 | Carr ................................ 128/653.1 |
| 4,784,147 | 11/1988 | Moshfeghi . |
| 4,957,000 | 9/1990 | Delpy et al. ..................... 128/653.1 |
| 5,198,776 | 3/1993 | Carr . |
| 5,285,772 | 2/1994 | Rattner . |
| 5,363,050 | 11/1994 | Guo et al. ........................ 128/653.1 |
| 5,383,455 | 1/1995 | Hagelauer . |
| 5,384,573 | 1/1995 | Turpin . |

Primary Examiner—Brian L. Casler
Attorney, Agent, or Firm—Dorn, McEachran, Jambor & Keating

[57] ABSTRACT

A system for detecting an incipient tumor in living tissue such as that of a human breast in accordance with differences in relative dielectric characteristics. A generator produces a non-ionizing electromagnetic input wave of preselected frequency, usually exceeding three gigahertz, and that input wave is used to illuminate the living tissue, being effectively focused into a small, discrete volume within the tissue to develop a non-ionizing electromagnetic wave at that position. The illumination location is moved over a portion of the living tissue in a predetermined scanning pattern. Scattered signal returns collected from the living tissue are collected to develop a scattered return signal. The scattered return signal is employed to detect any anomaly, caused by differences in relative dielectric characteristics, that is indicative of the presence of a tumor in the scanned living tissue.

27 Claims, 14 Drawing Sheets

NON-INVASIVE SYSTEM FOR BREAST CANCER DETECTION

This application is a continuation-in-part of U.S. Ser. No. 08/269,691, filed Jul. 1, 1994 now abandoned.

BACKGROUND OF THE INVENTION

Breast cancer is one of the leading causes of death for women. About one out of eight or nine women are expected to develop tumors of the breast, and about one out of sixteen to twenty are expected to die prematurely from breast cancer.

Mammography or other X-ray methods are currently most used for detection of breast cancers. However, every time a mammogram is taken, the patient incurs a small risk of having a breast tumor induced by the ionizing radiation properties of the X-rays used during the mammogram. Also, the process is costly and sometimes imprecise. Accordingly, the National Cancer Institute has not recommended mammograms for women under fifty years of age, who are not as likely to develop breast cancers as are older women. However, while only about twenty two percent of breast cancers occur in women under fifty, data suggests that breast cancer is more aggressive in pre-menopausal women. Furthermore, women under forty are getting the disease in increasing numbers—about eleven thousand annually now—and no one knows why.

Mammograms require interpretation by radiologists. One radiologist has said "I generally can spot cancers between five and ten millimeters in diameter. The prognosis is excellent then." However, about ten to fifteen percent of tumors of this size are not detected. One study showed major clinical disagreements for about one-third of the same mammograms that were interpreted by a group of radiologists. Further, many women find that undergoing a mammogram is a decidedly painful experience.

Thus, alternative methods to detect breast cancers are needed, especially those that do not entail added risks, that can detect tumors as small as two millimeters in diameter, that are not unduly unpleasant to the patient, and that can be used for mass screening. A screening system is needed because extensive studies have demonstrated that early detection of small breast tumors leads to the most effective treatment. While X-ray mammography can detect lesions of approximately five mm or larger, the accuracy may range between 30% and 75%, depending on the skill of the diagnostic radiologist. Repeated X-ray examinations, however, are not encouraged because these may become carcinogenic. These considerations, in addition to cost considerations, have led physicians to recommend that women wait until the age of fifty before having routine mammograms. One solution would be a non-ionizing, non-invasive, and low cost detection or screening method. It could greatly increase without hazard the number of patients examined and would identify those patients who need diagnostic X-ray examinations, where the added hazards and costs could be justified. Thus, there is a need for a low-cost, non-invasive, screening method.

About one in eight women develop breast cancers and about one in sixteen die prematurely from this disease. Despite strong encouragement, less than half of the millions of women who should be are routinely screened. Some of the reasons are cost and discomfort experienced during mammography. Other concerns are the additional risks associated with ionizing radiation, especially for routine exams for women under fifty. However, while only twenty two percent of breast cancers occur in women under fifty, data suggest that breast cancer is more aggressive in pre-menopausal women. A screening procedure need only identify breasts with abnormalities. The precision and imaging requirements associated with diagnostic purposes and treatment monitoring, while desirable, need not apply.

There are several generic detection methods: sonic, chemical, nuclear and non-ionizing electromagnetic. The sonic, chemical and nuclear (such as MRI) techniques have been under study for some time and, while some interesting approaches are being followed, none have been publicized as being available in the near future for low cost screening.

Non-ionizing electromagnetic methods have also been under investigation. Studies have considered the use of electromagnetic, non-ionizing methods to detect or image portions of the human body. An excellent summary of such activity is presented in a publication entitled "Medical Applications of Microwave Imaging", edited by L. E. Larsen and J. H. Jacobi, IEEE Press 1986.* These activities include microwave thermography, radar techniques to image biological tissues, microwave holography and tomography, video pulse radar, frequency modulation pulse compression techniques for biological imaging, microwave imaging with diffraction tomography, inverse scattering approaches, and medical imaging using an electrical impedance. The publications in this book contain about five hundred citations, some of which are duplicates. The technology cited not only includes electromagnetic disciplines, but also notes related studies in sonic imaging and seismic imaging. To update these data, the IEEE transactions on Medical Imaging, Biomedical Engineering, Microwave Theory and Techniques and Antennas and Propagation have been reviewed. Also surveyed was the publication Microwave Power and Engineering. This update has indicated little significant progress in the aforementioned electromagnetic techniques that would be important to detect \* See the list of references at the end of this specification. breast cancers. Breast cancer detection systems based on the concepts described in this specification were not presented.

Many important reasons exist for this lack of progress. In the case of microwave thermography, adequate depth of penetration, along with the required resolution, may not be realized, except for large cancers. In the case of holography, reflections at the skin-air interface tend to mask the desired returns from breast tumors beneath the skin. Further, illuminating the entire volume of a breast either requires excessive power (with possible biological hazards) or acceptance of poor signal-to-noise ratios. In the case of through-the-body electromagnetic techniques, such as tomography, the attenuation characteristics of the body are such that long wavelengths are usually used, with an attendant loss of resolution. Imaging by determining perturbations in body impedance caused by the presence of tumors as sensed by multi-electrode arrays have been either inadequate in sensitivity or subject to false alarms.

A millimeter wave FM radar weapons detection system developed and tested for the FAA (DTFA03-87-C-00056) by the inventor employed a 94 GHz FM radar operating with a 300 Mhz bandwidth. A half-meter diameter antenna with a half inch spot size focused the radiated 94 GHz energy through the air onto a possible passenger boarding an aircraft. This system successfully detected both metallic and plastic weapons, with an overall detection probability of 96.2%. The false alarm rate was 31.09%. It was hoped, initially, that the system could be used to detect breast cancers, since there was some empirical evidence suggested that the 94 GHz waves were penetrating the skin sufficiently that some portions of the shoulder blades could be resolved.

However, subsequent research has disclosed that the air-skin interface would not only enlarge the spot size, but would reflect a very substantial fraction of the impinging waveform.

To mitigate the resolution problem, a much higher frequency is needed to realize a usable spot size. However, the use of higher frequencies greatly increases the path attenuation of the penetrating energy, thereby introducing major design difficulties. These findings largely negated the use of this system for breast cancer detection. Nevertheless, the results of this FAA project suggested that at least some features of a millimeter wave weapons detection system, designed from existing data, could be revised and integrated into a successful prototype system for detecting breast tumors.

SUMMARY OF THE INVENTION

The objective of this invention is to provide a system to propagate non-ionizing electromagnetic waves having wavelengths not much greater than three times the circumference of the smallest tumor to be detected, preferably having wavelengths, in normal breast tissue, of the order of thirty millimeters or less and preferably of the order of ten millimeters. Propagation is effected without incurring intractable path losses, while at the same time being able to discern breast tumors of the order of three millimeters. The penetration is realized by: 1) avoiding interface reflections by employing media that have about the same dielectric constant as the breast tissues; 2) choosing a frequency (and wavelength) that readily penetrates normal breast tissue; and 3) providing means to extract tumor-scattered power from the applied or impinging power. The desired resolution is achieved by: 1) choosing a frequency such that its wavelength in breast tissue is comparable to the minimum size tumor to be detected; 2) using a wide aperture antenna that focuses the mmw energy at discrete points within the breast; and 3) relying on significant differences between the dielectric properties of the normal breast tissue and those of the breast tumors. Optimum operation is usually achieved at frequencies in the range of three to ninety gigahertz.

A principal feature of this invention includes means to introduce microwave or millimeter wave energy into a breast with a minimum of interface reflections and loss of resolution (or increased spot size). This is done by means of dielectric materials in the illuminator that have about the same relative dielectric constant as the breast tissue and by use of gels, liquids, slurries and/or solids that have a similar relative dielectric constant around the breast to further suppress interface gaps that could cause reflections and loss of resolution.

Another important feature is the selection of a band of operating frequencies wherein the attenuation of the propagating energy in a non-lactating breast is relatively small, preferably of the order of 1.5 to 15 dB/cm, in combination with an antenna or illuminator aperture size that produces a spot size preferably in a range of about 2.5 to 12 millimeters in normal, non-lactating breast tissue.

Another important feature comprises the use of a wide aperture scanning system. The construction of the scanner is such that the focus of the energy introduced is scanned at different depths, at depth increments comparable to the depth of focus, to provide a quasi-three-dimensional picture of the backscattered returns. To overcome path anomalies that might cause ambiguous results, different scanning patterns can be employed to average out such effects. Also, advantage can be taken of other features inherent in electromagnetic propagation systems, such as the use of different polarization effects, including circular polarization, and enhancement of the backscatter cross-section wherein the circumference of the tumor is equal to the wavelength. Also, use of forward and side scatter can be employed to help resolve ambiguities.

Yet another important feature employs techniques that aid in separating the desired scattered returns from a tumor from those originating either directly from the impinging waveform or from spurious reflections from scatterers of no interest. This may be done by "passive methods", such as employed in microwave circuits (magic tees or circulators) or by tumor-unique scattering phenomena (wherein the polarization, side-scatter, forward-scatter returns or tumor-induced resonant effects are utilized). Additionally, "active methods", such as time-gating or pulse-compression methods (sometimes employed in modern radar systems) may also be used.

Another feature of this invention is the use of a stepped frequency technique to develop a synthetic time domain response. As opposed to applying a large amplitude short duration pulse and then using time-gating or the use of swept frequency FM "Chirp" radar pulse compression methods, the stepped or swept frequency input impedance method can be more easily implemented. The dwell time at each frequency can be adjusted to give adequate signal-to-noise ratios, digital processing and control can be used, and the hardware needed to implement this method is available.

Another feature of this invention is the use of confocal techniques, where the focal point of the illumination and the focal point of the collection system are nearly the same point in the breast tissue. Such arrangements suppress the effects of incidental sources of scattering that might occur at locations outside the common focal point.

Another feature is the combined use of the confocal method with the stepped frequency synthetic time domain method, especially for detecting anomalies at depth. On one hand, the confocal method is most effective at shallow depths, and loses its ability to suppress incidental scattering for deeper tumors. The synthetic time domain method, if used separately from the confocal arrangement with more commonly available antennas, will generate back scatter from sources over a wide area. Scatter from such incidental sources could mask the desired returns from any tumor. However, the combined use will provide more benefit than would be suggested by the performance of each subsystem separately. The confocal method suppresses clutter sources (incidental scattering) that are transverse to the direction of propagation and the time domain system suppresses clutter sources in the longitudinal direction.

Another feature of the invention is convenience to conduct screening. As opposed to other microwave methods that require access to nearly all sides of the breast, the method noted here needs access to only one side.

Another feature of the invention is that it can provide non-hazardous screening functions, such that breasts, over time, can be compared to detect abnormalities that would not otherwise be possible with an ionizing approach or more expensive methods, such as MRI.

One version of the invention includes a quasi holographic technique wherein the amplitude and phase of the scattered returns are compared to a reference signal and subsequently used to form some type of three dimensional display. A modified interferometer technique can be used to do this. The interferometer provides 3-D displays of the backscattered power and the cumulative phase shift of the returns with respect to a reference point.

BRIEF DESCRIPTION OF THE DRAWINGS

The following figures are used to explain the concepts and design of the breast cancer detection system of the invention.

DESCRIPTION OF THE PREFERRED EMBODIMENTS

The use of electromagnetic microwave or millimeter waves offers several advantages over x-ray mammography in detecting incipient breast cancers. (To simplify this discussion both microwave and millimeter wavelength regimes will be referred to as mm waves, or mmw.) Non-ionizing electromagnetic systems can be operated at sufficiently low levels so as to preclude biological hazards. A contrast ratio of the order of 20:1 is potentially usable for mm waves in tissue, whereas there is less than a few per cent range of densities for X-rays for soft tissue. The tissue-mm wave interaction also exhibits additional phenomena that can be drawn upon to enhance the performance. For example, when the diameter of a highly conducting sphere (e.g., an incipient cancer) is of the order of a wavelength in the breast tissue, a resonance effect occurs that increases the effective scattering cross-section of the tumor. If the tumor is non-spherical, then the polarization of the scattered waves may be different than that of the impinging waveform. In some cases, side-scattered or forward scattered energy can also be utilized. For purposes of this specification, tissue-mm waves are defined in terms of wavelength in a medium having a dielectric constant like that of breast tissue, not air. Thus, the operating frequency for an electromagnetic wave source used in the inventive system is preferably in the range of three to ninety GHz.

Other than the use of millimeter wave and microwave thermography to detect breast cancers, there has been little activity toward use of such mm wave approaches to detect breast cancers. As noted earlier, some of the problems that have to be overcome are formidable. First, simply flooding the torso of a female with mmw energy introduces numerous problems. How does one single out the scattered return from a three millimeter circumference tumor out of the immensely larger scattered returns from the torso? How is the defocusing effect of the air-skin interface overcome? Is the breast tissue sufficiently transparent, at mmw frequencies, to propagate energy into and out of the breast? Are the dielectric properties of the tumors sufficiently different from normal breast tissue for effective detection of small (e.g., three mm circumference) incipient cancers?

To understand the invention and its novel features, the basic concept will first be briefly described. Next, the ability of the millimeter wave electromagnetic energy to penetrate normal breast tissues will be demonstrated. Then, the special equipment and operating conditions will be described to realize the needed high resolution simultaneously with good penetration.

Figure 1A:
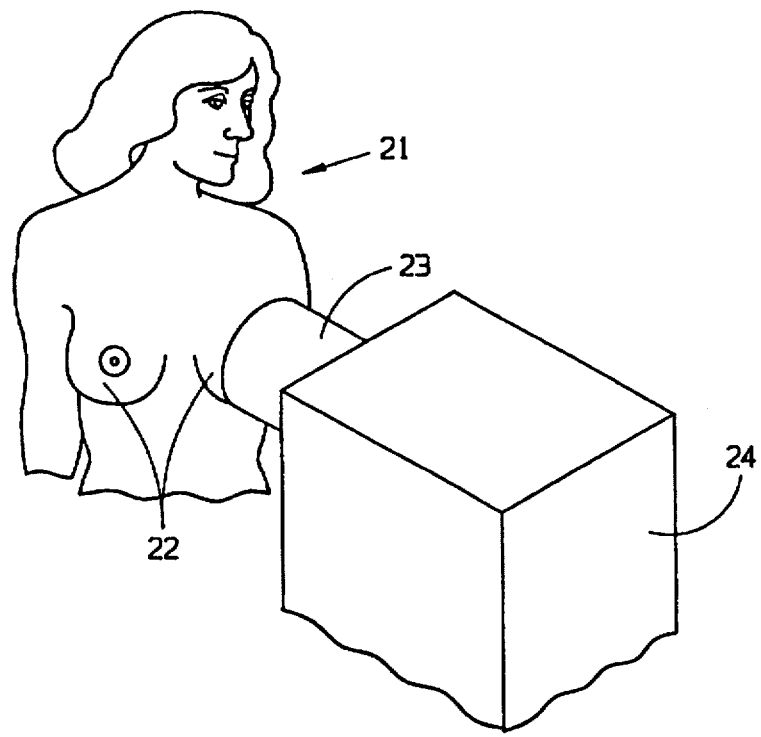
FIG. 1A, is a conceptual view an active millimeter wave breast cancer detection system, with a patient.
Figure 1B:
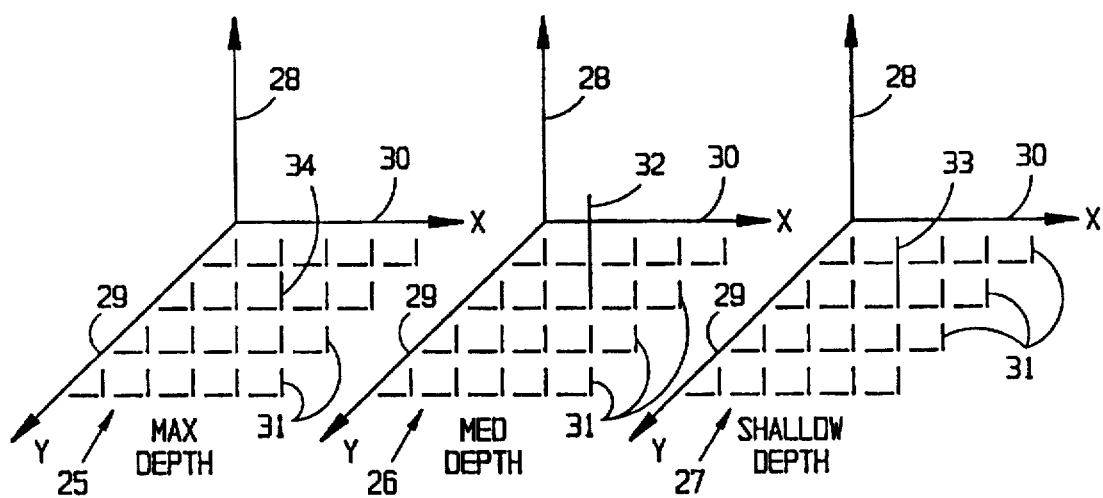
FIG. 1B illustrates displays for plural focal lengths, with the generalized system of FIG. 1A.

FIGS. 1A and 1B illustrate the basic concepts. FIG. 1A illustrates, on a conceptual basis, possible prototype equipment. The patient 21 arranges one of her breasts 22 to contact an illuminator 23 as shown. Mm waves are generated within the equipment housing 24. These mm waves are then propagated into the selected breast 22 as a refracted or reflected electromagnetic mm wave that is focused at a predetermined point or volume (voxel) within the breast. This is done by means of a unique combination of an interface and focusing apparatus, as described hereinafter. Further apparatus is used to cause the focal point of the beam to scan different small volumes or voxels within the breast. When this happens, the scattered mmw energy from any tumor present in the breast becomes much larger that other scattering sources, since the dielectric properties of a tumor are radically different than that of the breast tissue. The scattered returns may be collected as backscattered power via the same interface and focusing apparatus that is used to propagate the mmw power into the breast. The collected power can then be processed by either analog or digital methods to form an image of the tumor.

A stepped FM sweep similar to pulse compression in "Chirp" radar to synthesize a time domain response to isolate shallow from in-depth scattering can be used to mitigate the effects of heterogeneity in the dielectric characteristic of the breast. The functional goal of the combined confocal and time-domain features is to isolate the returns from tumors from spurious returns generated by heterogeneity in adjacent normal tissues.

Electromagnetic waves in the mm wave region, in combination with the shape and dielectric properties of tumors in the breast, offer additional methods to detect the presence of a tumor beyond using just simple back, forward, or side scatter. In some cases, the tumor can exhibit both internal and external electromagnetic resonances which are unique to its presence. Such resonances can be detected by varying the mmw frequency, by observing changes in polarization, by observing transient responses to an impulse function, or by noting changes in the ratio of the forward, side, backscattered and spurious returns. If the geometry of the tumor is asymmetrical, then the plane of polarization of the scattered energy may change; this change can be used to confirm the presence of a small tumor.

The amount of collected backscattered energy and its accumulated phase shift (or time of flight or round trip time delay) can be presented in a 3-D format, as shown generally in FIG. 1B. For illustrative purposes, it is assumed that the impinging energy can be selectively and sharply focused into three vertical planes that are parallel to the patient's chest, wherein the x-y planes at maximum depth 25, medium depth 26, and shallow depth 27 are shown. The three coordinates show the backscatter returns 28, the "x" coordinate 30 and the "y" coordinate 29. Small vertical lines 31 are shown for numerous combinations of x and y coordinates.

The amplitudes or heights of most of these lines 31 are proportional to the non-target returns that can arise from, for example, the tissues that surround the rib cage. Note that a very large return 32 exists in the center of the medium depth display 26. This large return 32 is assumed to arise from a tumor that is at the focus of the impinging energy in the medium depth plane 26. In the center of the Shallow plane 27 there is a somewhat smaller response 33 caused by the tumor intercepting and only scattering a small portion of the impinging beam. Note that in the center of the deeper plane 25, the return 34 is smaller because, it is assumed, the focused energy has largely been scattered by the tumor in the medium depth plane 26 before it arrives at the center of the deeper plane 25.

Figure 2:
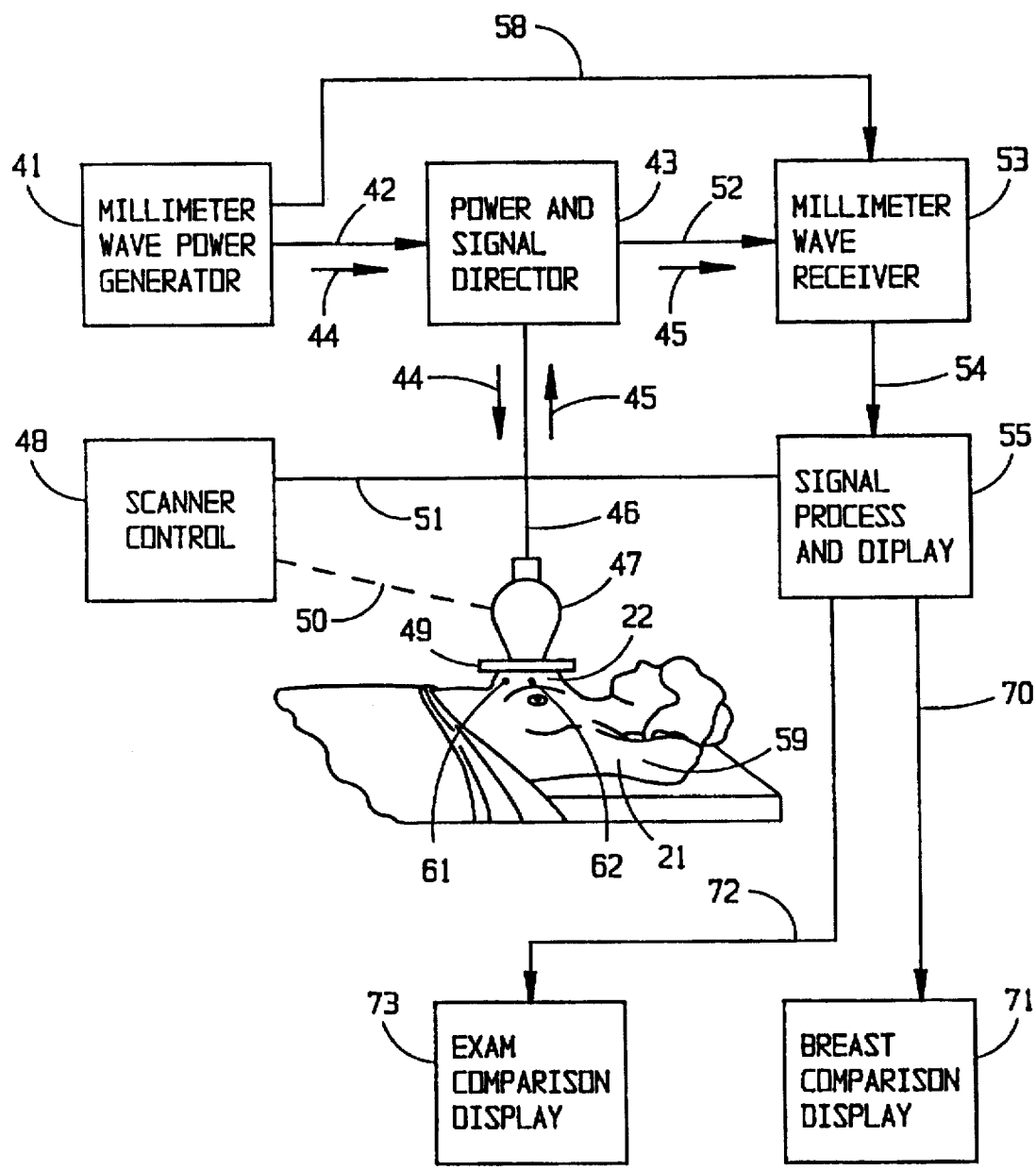
FIG. 2 is a simplified block diagram that illustrates the principal functions of a mmw breast cancer detection system constructed in accordance with the invention.

FIG. 2 presents a block diagram that illustrates the principal functions of the mmw breast cancer detection and imaging apparatus. Microwave or millimeter wave power is generated by a mmw power generator 41. This power is supplied to a power and signal director 43 via a cable or waveguide 42. The power output 44 from the director 43 flows to an illuminator 47 via a waveguide 46. The illuminator 47, via a scanning plate 49 of dielectric material, causes the power to be focused at a point 62 within the breast 22. A scan control 48, via a mechanical connection 50, causes the illuminator 47 to move along the plate 49 in a predetermined scanning pattern. When the focus of the power encounters a tumor 61, backscattered power 45 is collected by illuminator 47 and is returned, via waveguide 46, to the power and signal director 43.

To prevent the applied power from swamping or masking returns from the tumor 61, means must be included to extract the desired return or signal from the tumor from the applied power. The initial function of the director 43 is to direct the mmw power output 44 from the generator 41 to the focusing illuminator 47 through the cable or waveguide 46. The director 43 also is employed to extract the tumor-scattered returns 45 that are collected by the focusing illuminator 47. The extracted returns 45 from the power and signal director 43 are applied to a mmw receiver 53 via a cable or waveguide 52.

The requisite directing action of the director 43 can be realized by several "passive" means, such as a balanced bridge circuit or magic tee, a directional coupler, or a circulator (see Ramo et al. (1965) Fields and Waves in Communication Electronics, John Wiley and Sons, New York, sections 11.17, 11.8 and 9.16). "Active" means of separating the applied power 44 from the tumor-scattered power 45 are possible in the time domain. For example, very short duration pulses of mmw energy can be applied and the returns separated by time gating methods. Other "active" methods currently employed in some modern radar systems can be used, such as pulse compression, chirp or frequency modulation radar; see Skolnik. Introduction to Modern Radar Systems, McGraw-Hill (1980).

The focusing illuminator 47 of FIG. 2 has several functions. One principal function is to focus the applied power at a predetermined point within the breast 22. Another principal function is to condition the spatial distribution of dielectric material to enhance resolution. Yet another function is to suppress dielectric and electrical interface reflections that could mask the scattered returns from a possible tumor 61 in the breast 22 of the patient 21. These functions may be done by matching the wave propagation characteristic or dielectric constant of the illuminator 47 and the scanning plate 49 to that of the breast 22 and also matching the electrical interface between the cable/waveguide 46 and the focusing illuminator 47 by means of electrical matching networks, such as the mmw equivalent of a "pi" or "tee" or "L" network.

The scan control 48 controls the position of the focal point 62 of the illuminator 47 via a mechanical connection 50 that slides the illuminator 47 over the scanning plate 49 in a predetermined scanning pattern. This action provides x and y positioning of the focal point. Alternatively, other techniques may be used in conjunction with the scan control 48 to create an apparent focal point, such as by means of phased arrays or synthetic aperture methods.

The scattered returns 45 from a possible tumor or other scattering sources are applied to the mmw receiver 53 via the wave guide 52 and the power and signal director 43. This mmw receiver 53 may be a conventional heterodyne receiver that provides an output proportional to the power received. Alternatively, using a waveguide 58 connected from the mmw generator 41 to the receiver 53, a reference signal can be compared with the return signal 45 to develop composite phase and amplitude data.

The outputs from the mmw receiver 53 are supplied, via a cable 54, to a signal processing and display unit 55. This unit 55, with a further input from the scan control 48 via a cable 51, processes the received data into a suitable display, such as illustrated in FIG. 1B.

In the case of screening for breast cancer, the performance requirements can be relaxed, since the detection of an abnormality is the real goal. This can be done by comparing the returns from one breast with the other. In addition, year-to-year examination data can be compared. As shown in FIG. 2, information via cable bundle 70 on the returns from each breast can be compared; see block 71. Cable bundle 72 carries similar data for storage and subsequent comparison via block 73 after each yearly examination.

Various known comparison techniques can be used for this purpose. For example, a transparency of a positive image taken of the breast at one time may be overlain with a transparency of a negative image taken at a later time. Any significant return on the positive is presented as a very light gray area in the refrence-gray background and the return taken a later time is displayed as a dark area in the reference-gray background. If no change has occurred, the light gray area on the positive and the dark gray area on the negative will tend to cancel and result in a nearly reference-gray density. If some change has occurred in a specific area, the images will not cancel in this region, and the abnormality will be indicated as either a darker or lighter region in the reference-gray background. A similar process can be done digitally, and the difference displayed visually in a two dimensional display for a given "slice" or depth into the breast.

Figure 3:
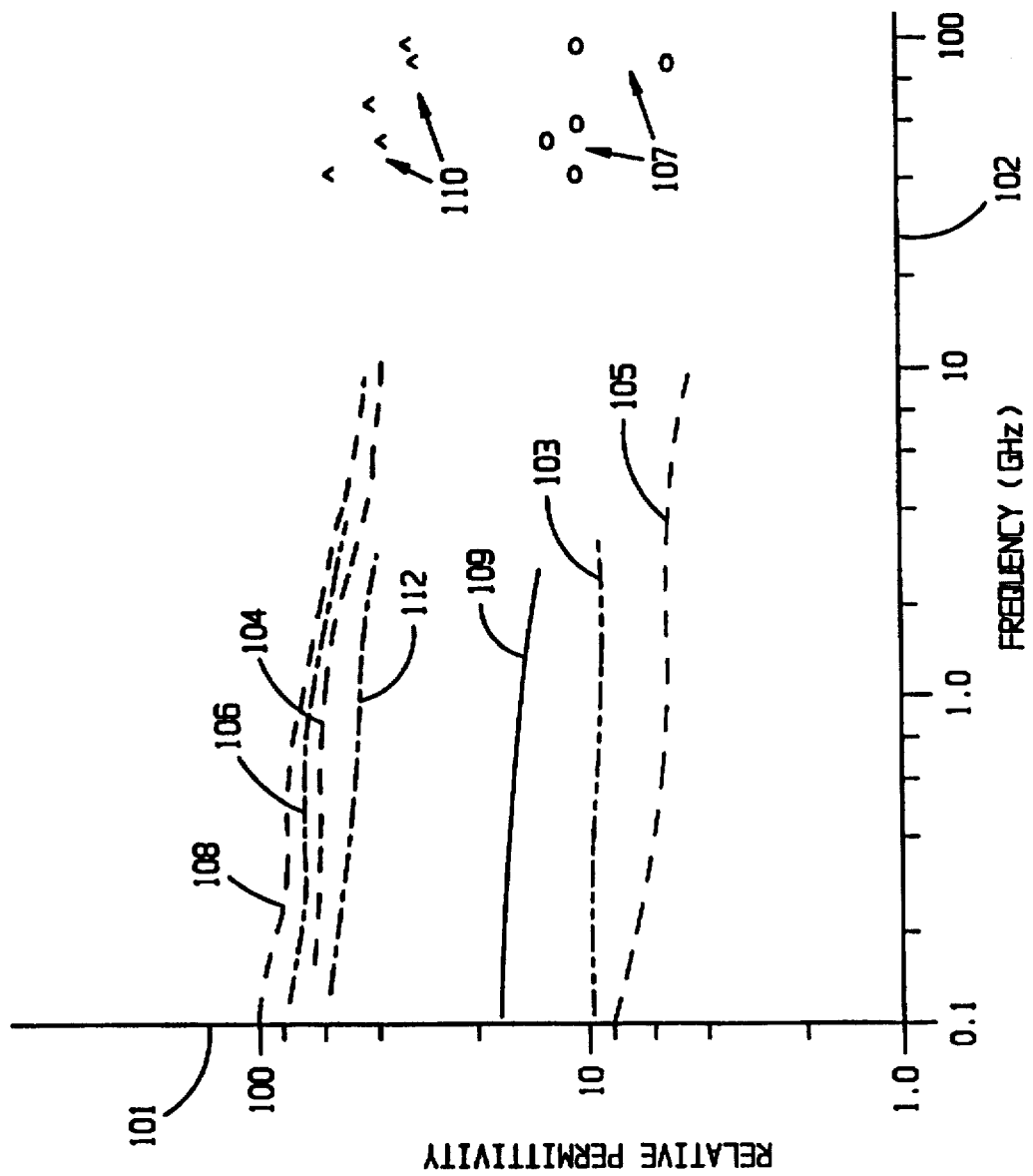
FIG. 3 is a graph of relative dielectric constants of muscle, fat, breast tissue and breast cancer as reported by various investigators.
Figure 4:
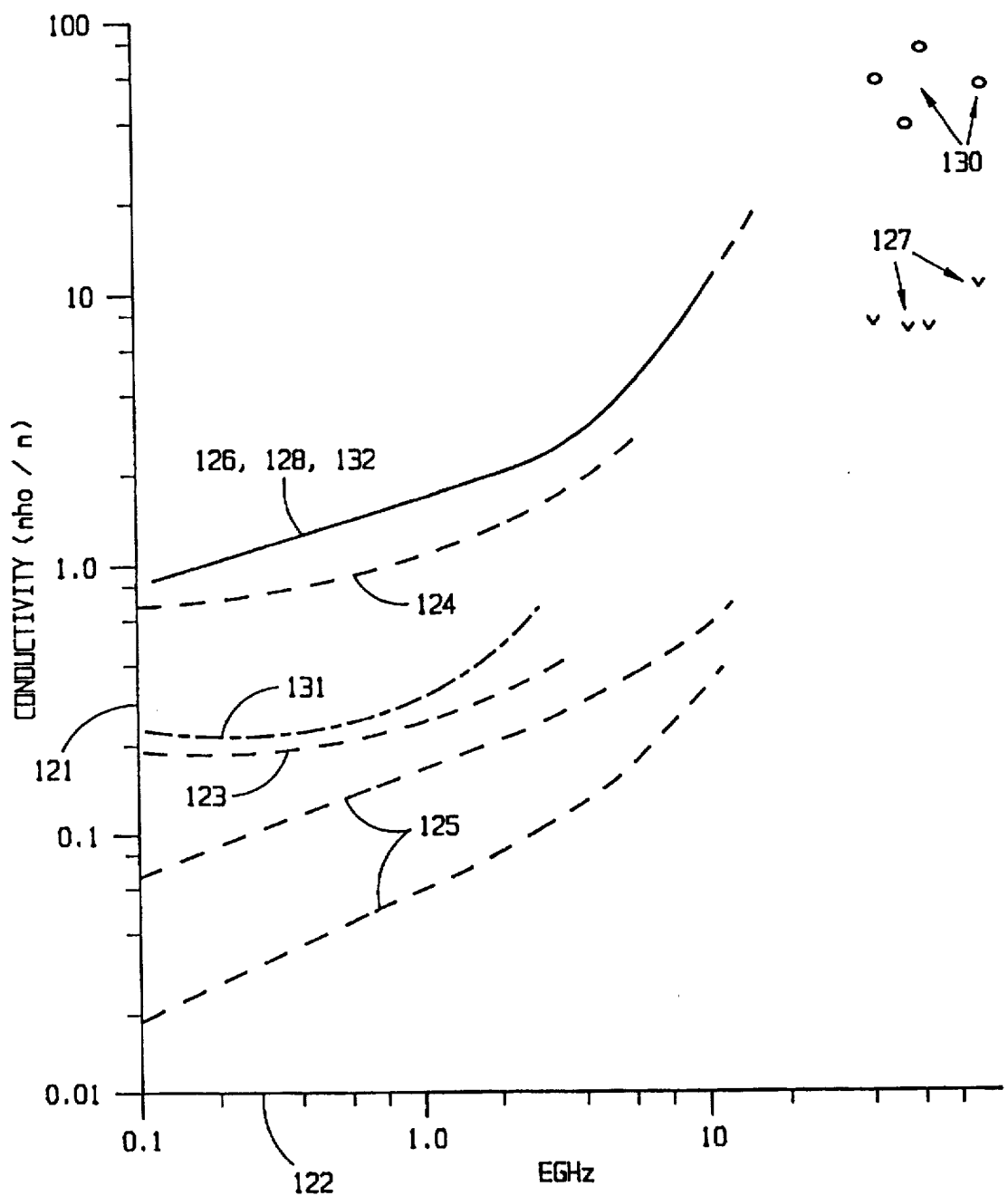
FIG. 4 is a graph of conductivity of muscle, fat, breast tissue and breast cancers as reported by various investigators.
Figure 5:
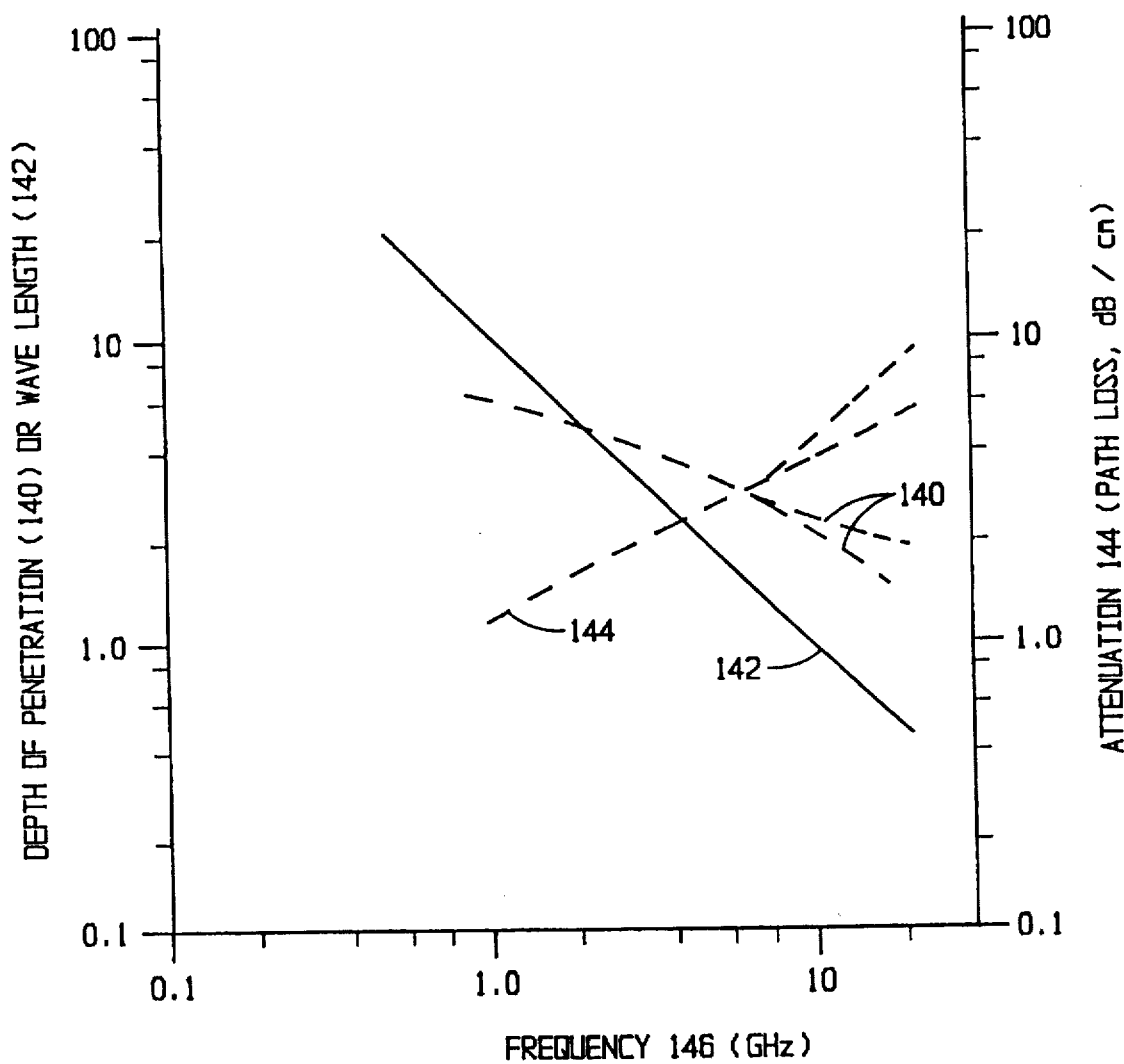
FIG. 5 is a graph of attenuation, wavelength, and depth of penetration in normal breast tissue as a function of frequency, based on the data presented in FIGS. 3 and 4.

FIGS. 3, 4 and 5 provide data that demonstrate that non-lactating breast tissue has different dielectric properties than either tumors or muscle tissues. Moreover, the attenuation of mm waves in such breast tissue is not excessive in the 5 to 15 GHz region and hence permits reasonable operating conditions for "passive" power and signal directors. Additional attenuation can be tolerated by the use of "active" power and signal directors such that operation up to sixty GHz is possible.

FIG. 3 summarizes data on relative permittivity, scale 101, as a function of frequency, scale 102. These data demonstrate that the relative dielectric properties of low-water-content tissues and normal breast tissues are significantly lower than for high-water-content tissues and tumors, either human or non-human. The low-water content data for curve 103 were developed by Chaudhary (1984) for human breast tumors. Johnson (1972) developed the data for curve 105 for fat, bone and low-water content tissue. Edrich (1976) generated the data for cattle fat, shown in the curve 107. Burdette (1986) generated in vivo data for canine fat, illustrated in a curve 109. The high-water-content data for another curve 104 was developed by Chaudhary (1984) for human breast tumors. Johnson (1972) developed data for muscle and high water content tissues, shown in a curve 106. Rogers (1983) generated the data, shown in a curve 108, for mouse tumors. Edrich (1986) collected data for canine muscle, illustrated in a curve 110. Burdette (1986) provided in vivo data, shown in curve 112, for canine muscle tissue. Note that in the case of muscle or tumor tissues, the relative dielectric constant is of the order of forty or more, depending on the frequency. In the case of low-water-content tissues, such as breast or fat, the dielectric constant is in the order of five to ten, as measured for in vitro studies. The in vivo measurements of Burdette (1986), shown in curves 109 and 112, show an approximate increase by a factor of two in the relative permittivity over the data developed by Johnson (1972), curves 105 and 106. The in vitro breast tissue measurements by Chaudhary (1984), curves 103 and 104, fall somewhat in between the in vitro values developed by Johnson (1972) and the in vivo measurements of Burdette (1986).

FIG. 4 presents similar data on the conductivity of both low and high-water-content tissues. The conductivity in mhos/meter, scale 121, is the ordinate and the frequency, curve 122, is the abscissa. The low-water-content tissues are human breast tissues, shown in a curve 123 derived from Chaudhary (1984). The low-water-content fat and bone of the curve 125 is from Johnson (1972). Cattle fat, shown in a curve 127 is from Edrich (1986). The high-water-content tissues of the curve 124 are human breast tumors, data by Chaudhary (1984). High-water-content muscle tissue is in a curve 126, data by Johnson (1972). Mouse tumors, shown in a curve 128, are from Rogers (1983). Rat muscle data for a curve 130 is derived from Edrich (1986). Canine fat data are presented in a curve 131 from Burdette (1980), and canine muscle data in a curve 132 taken from Burdette 1980). Note that conductivity, as a function of frequency, tends to increase substantially above 6 GHz and that the 40 to 90 GHz measurements of Edrich (curves 127 and 130) tend to fall in line with the trends established by measurement made up to 10 GHz.

Based on the data presented in FIGS. 3 and 4, FIG. 5 shows the depth of penetration 140, wavelength 142, and attenuation 144 as a function of frequency 146 for the propagation of millimeter waves in non-lactating breast tissue. Above ten GHz, some uncertainty associated with the trend extrapolation is suggested by the range of possible values of the penetration depth 140 or attenuation 144. A value of nine was used for the relative dielectric constant and the extrapolated values of Chaudhary (relative to the data developed by Johnson) from FIG. 4 were used for the conductivity. From these data, it is seen that the breast tissue behaves as a lossy dielectric for frequencies substantially exceeding five GHz, wherein $\omega=2\pi F$ and $\epsilon=\epsilon_o\epsilon_r$ (permittivity of free space)×(relative dielectric constant), $\sigma$ is the conductivity, $\mu$ is the permeability, f is the frequency, $\lambda$ is the wavelength, and $\delta$ is the depth of penetration (see Ramo (1965) page 334 Sec. 6.05).

Since $\omega\epsilon>>\sigma$, the approximate lossy dielectric equations are as follows:

$$\lambda=(\mu\epsilon)^{-\frac{1}{2}} \tag{1}$$

$$\delta=2[\sigma(\mu\epsilon)^{1/2}]^- \tag{2}$$

This defines the generic feasibility of the system to be described hereinafter. There are two requirements that must be met. First, the total path loss attenuation (in and out) should be substantially less than the dynamic range, typically in the order of 100 dB, wherein the dynamic range is defined in dB as equal to: 10 log[(largest signal power)/ (smallest detectable signal power)]. Second, the wavelength in the irradiation apparatus (illuminator 47) and in the breast of the patient should be sufficiently small so that small tumors can be resolved. This, for the system discussed here, requires that, preferably, the wavelength in illuminator 47 and in the breast tissue should not exceed two or three times the circumference of the smallest tumor. If an operating frequency of 15 GHz is chosen for a passive power and signal detector, it is seen that the path loss is about 5 dB/cm, or 50 dB total path loss, in and out, for a 5 cm path length. The wavelength at 15 GHz is about 0.6 cm, which is about equal to the diameter of the smaller tumors.

Figure 6:
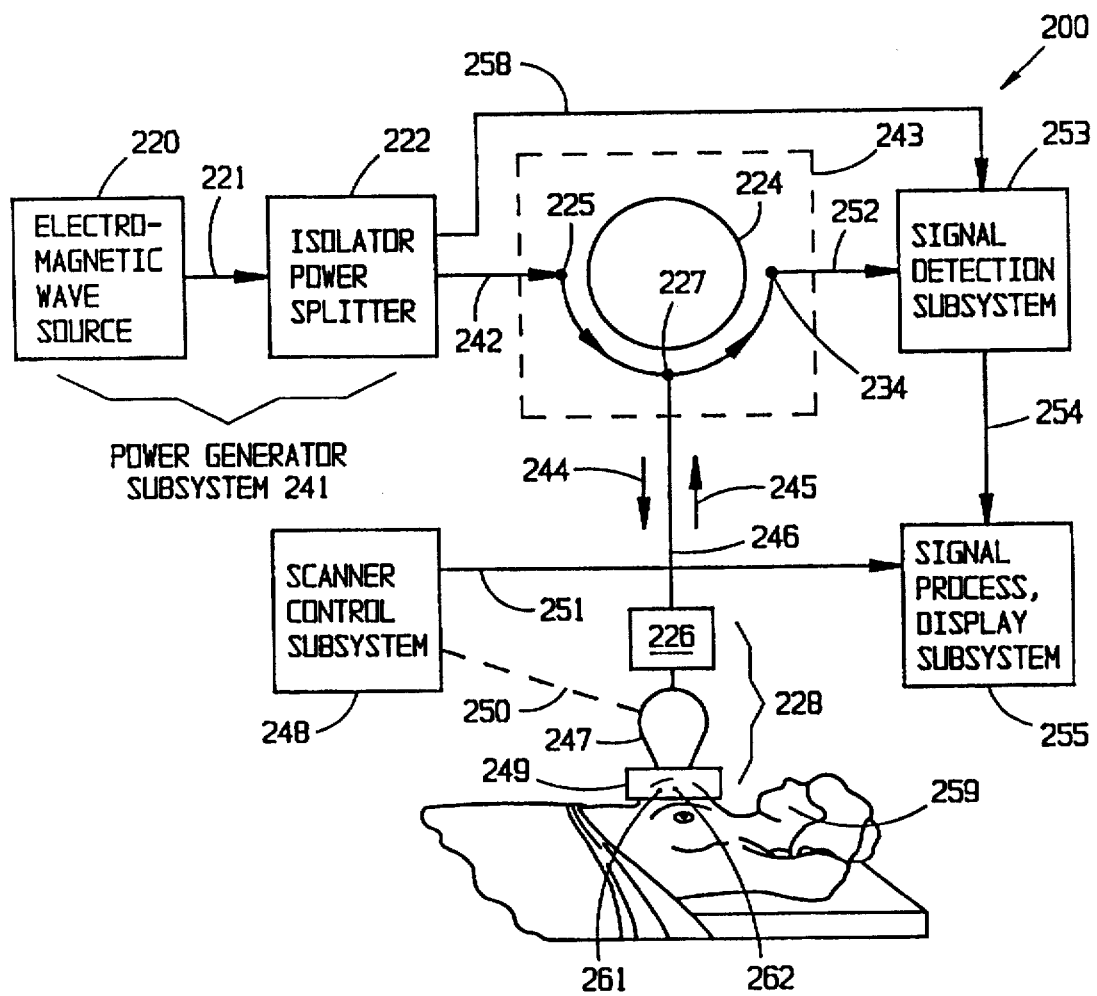
FIG. 6 is a block diagram of a mmw breast cancer detection system, according to the invention, that employs a "passive" signal separation technique in combination with a conventional heterodyne receiver to detect tumor-scattered returns.

FIG. 6 illustrates a functional block diagram of a microwave breast cancer detection and imaging system 200 that employs a conventional heterodyne receiver. System 200 comprises the following subsystems: a millimeter power generator subsystem 241, a passive power and signal director 243, a focusing illuminator subsystem 228, a heterodyne receiver 253 employed for signal detection, a scanner control 248, and a signal processing and display subsystem 255.

Electromagnetic wave energy flows, via the power and signal director 243, from the power generation subsystem 241 to the illuminator subsystem 228. The illuminator subsystem 228 comprises three major parts: a beam focusing apparatus 247, a matching network 226, and a dielectric equalizing interface 249. The focusing apparatus 247 of the illuminator 228 focuses the energy into a small point 262 within the breast of the patient 259. The scanner 248, through a mechanical connection 250, controls the location of the focal point 262 in three dimensions (3-D) such that the focal point 262 is progressively positioned into each voxel (smallest volume element) of the breast under consideration. When the focal point encounters a tumor 261, the scattered returns are substantially increased, since the electrical permeability and conductivity of the tumor is greater than similar parameters for breast tissue. The scattered returns are collected by the illuminator 247 of subsystem 228 and then the scattered power (arrow 245) is supplied via the matching network 226 and the power and signal director 243 to the detection subsystem 253.

The scattered power 245 is separated from the impinging power 244 (supplied to the illuminator) by means of a circulator 224 within the power and signal director 243. A discussion of each of the aforementioned subsystems follows.

The power generation and control subsystem 241 is comprised of two functional blocks: an electromagnetic wave power source 220 connected via a cable 221 to an isolator and power splitter 222. This, in turn, is connected, via a cable 242, to the power input port 225 of the circulator 224 in the power and signal director 243. The power output and backscattered input port 227 of the circulator 224 is connected, via a cable 246, to the matching network 226 at the input of the illuminator subsystem 228. The output port 234 of the circulator 224 is connected to the signal processor subsystem via a cable 252.

Many of the functions of these components are obvious. The isolator/power splitter 222 electrically isolates the power source 220 from any load variations that might be introduced by the circulator 224, the matching network 226, or other components of the illuminator subsystem 228. The function of the circulator 224 is to extract the backscattered returns from the applied power. Otherwise, the high level of the power applied to the illuminator subsystem 228 would tend to mask the desired scattered returns. Thus, the electromagnetic input signal injected into port 225 is directed out of port 227 and thence to the matching network 226. The backscattered returns (from the matching network 226) that are applied to port 227 appear at port 234, wherein the amplitude of the applied power is greatly suppressed. The purpose of the matching network 226 in subsystem 228 is to suppress reflections that might take place at the interfaces of different dielectric materials or where some wave impedance discontinuity occurs in the illuminator subsystem 228.

The performance requirements for the signal detection system 253 are not too stringent. The simplest version may use a simple heterodyne receiver as an RF voltmeter to measure the output of the circulator 224 at port 234. A reference signal from the power generation subsystem 241 can be supplied to the hetrodyne receiver 253 via a conductor 258 to stabilize the local oscillators in the receiver.

Figure 7:
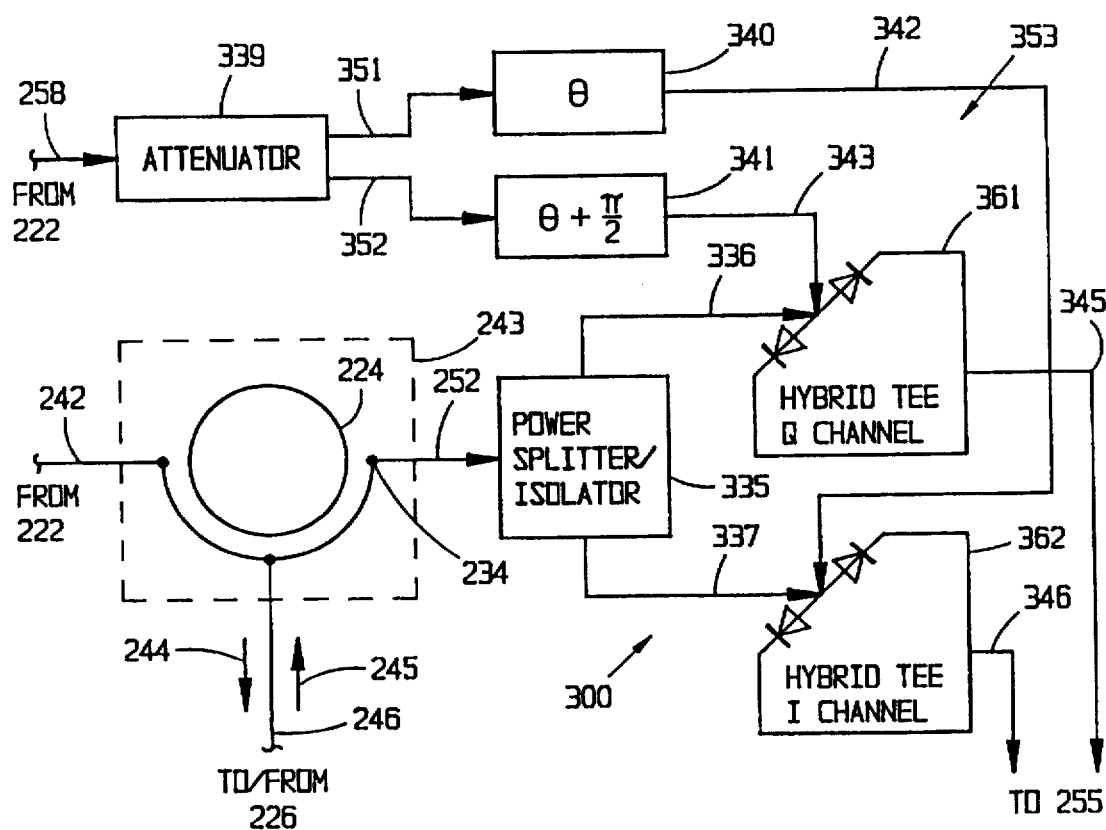
FIG. 7 is a block diagram of a breast cancer detection system, again according to the invention, that employs phase coherent detection.

Other versions of the invention, such as the system 300 shown in FIG. 7, offer additional signal processing options. The system 300 of FIG. 7 illustrates the use of two synchronous receivers or detectors in a modification of the system of FIG. 6 in which only the signal detection subsystem is changed, with subsystem 253 of FIG. 6 replaced by a dual subsystem 353 that includes two hybrid tee synchroneous detectors 361 and 362. The power splitter 222 (FIG. 6) provides a reference signal, on conductor 258 (FIG. 7) to system 353 as well as to the power and signal director 243. Each of the hybrid tee devices 361 and 362 forms a product between the applied input signal and the composite backscattered returns. However, one of the reference waveforms is shifted ninety degrees with respect to the other reference waveform; the following relationships result, where:

$\omega$ is the angular frequency of the millimeter waves;

$\theta$ is an arbitrary reference fixed phase angle;

$\lambda$ is the wavelength;

$\chi$ is the path length from the scatterer to the hybrid tee;

$\beta$ is the propagation phase constant and $\beta=2\pi/\lambda$;

$\chi\beta$ is the accumulated phase shift.

The output from each of the hybrid tees 361,362 is the product of the returned, scattered waveform and the reference waveform. Considering just the low frequency components of such products, the output of each of the hybrid tees is as follows:

$$A \cos [\omega t+\theta-2\chi\beta] \cos [\omega t+\theta]=A/2[\cos(-2\chi\beta)+\text{high freq. component}] \quad (3)$$

$$A \cos [\omega t+\theta-2\chi\beta]\cos [\omega t+\theta-\pi/2]=A/2[\sin(-2\chi\beta)]+\text{high freq. component} \quad (4)$$

The outputs can be defined as an in phase "I" vector component and a quadrature or "Q" vector component. These are combined as vectors so the phase angle of the combined vector becomes $\tan^{-1}(2\chi\beta)$. Typically, when no tumor is at the focal point 262 (FIG. 6), the backscatter from the chest tissue-lung interface can be assumed to form the zero reference distance for $\chi$. During scanning, the focal point may begin to encounter a tumor that is spaced a few or more millimeter wavelengths away from the chest muscles. When this happens, the effective distance $\chi$ progressively decreases, thereby causing the equivalent phase angle to rotate counter-clockwise. The number of rotations can be counted to develop the total accumulated phase angle change. The above relationships can be manipulated to present an accumulated path delay presentation that is responsive to the approximate distance of the scatterer from the illuminator. Such an option can be valuable in confirming the presence of a weak scatterer and can provide confirming location data for a strong scatter.

The dual receiver system depicted in FIG. 7 draws the reference waveforms from the isolator-power splitter 222 via cable 258. An attenuator-power splitter 339 is used to reduce the amplitude of the waveform presented to the two phase shifters 340 and 341 via appropriate cables or other conductors 352 and 351. The output waveform of phase shifter 341 is advanced or retarded ninety degrees relative to phase shifter 340 to provide the desired quadrature relationship. The quadrature reference waveforms from circuits 340 and 341 are applied, via cables 342 and 343, to the hybrid tees 362 and 361, respectively. The output of port 234 of the circulator 224 supplies the power from the backscattered returns, via cable 252, to the power splitter-isolator 335. This circuit 335 diverts the return signal equally into cables 336 and 337, thus supplying the backscattered signals to the hybrid tees 361 and 362. These tees 361 and 362 each form a product between the reference waveform (from conductors 343 and 342, respectively) and the backscattered signals (on lines 336 and 337, respectively). The low frequency output from these two devices 361 and 362, on cables 345 and 346, provides critical inputs to the signal processor and display subsystem 255 (FIG. 6). Other variations of the above technique may be used to improve the signal-to-noise ratio, such as modulating the reference waveforms with another frequency well above the highest frequency of interest in the detected backscattered return. This removes the output signal well away from the troublesome shot noise that occurs at very low frequencies.

The scanner control subsystems 48 and 248 (FIGS. 2 and control how the breast of the patient is scanned. In the case of the prototype system of FIG. 2, scanner control 48 controls the x and the y positions of an ellipsoidal reflecting antenna 47, which may be the antenna 170 shown in FIG. 10. Several antennas of different focal lengths may be used to access the location of a tumor. The scanner control (48 or 248) is mechanically connected to the illuminator (47 or 247) and to the signal processing unit (55 or 255) in each of the described systems of FIGS. 2 and 6. Phased arrays (not shown) could be used instead of a mechanically positioned illuminator to realize approximately the same scanning performance. Other methods, particularly techniques that synthesize large aperture antennas, could also be used.

In any of the described systems the signal processing and display subsystem (e.g., subsystem 255 in FIG. 6) can employ any number of processing or display methods so as to suitably display the scatter returns. It should be noted that since the scatter waveforms are referenced to the initial unperturbed electromagnetic wave illumination, quasi-holographic processing techniques can be considered.

Figure 8:
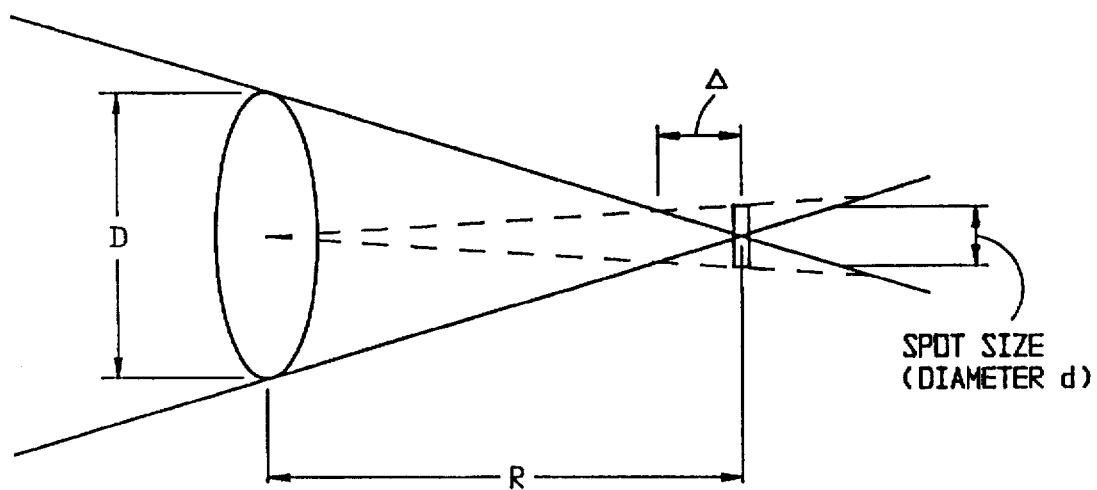
FIG. 8 is a diagram of resolution (or spot size) and depth of focus as functions of the diameter of an aperture or lens and of wavelength.

FIG. 8 defines the parameters needed to determine the spot size, including the diameter of the aperture D, the focal distance R, the spot diameter d, and the wavelength $\lambda$ of the millimeter wave in the media. See Kay (1966) and Smith (1966) for more complete development of relationships. Here, the spot size becomes:

$$d = 2R\lambda/D \qquad (5)$$

As was noted earlier in regard to FIG. 5, reasonable penetration losses of about five dB/cm occur for wavelengths of the order of six mm. Thus, if tumors in the order of three mm in circumference are to be resolved, the beam width or spot size should not exceed the tumor circumference by much more than a factor of three. Preferably, for improved spatial resolution, the wavelength should not exceed the tumor circumference by a factor of three. To achieve a spot diameter of 6 mm, the ratio of the focal distance R to the aperture diameter, D should be about 0.5.

Another design consideration is the depth of field $\Delta$, as related to the aforementioned parameters and the apparent angle of resolution $\Phi$. Thus the depth of field becomes:

$$\Delta = [R^2 \Phi]/[D \pm R\Phi], \text{ where } \Phi = d/R \qquad (6)$$

Again, to obtain good spatial discrimination, the focal distance R should be small compared to the aperture diameter D.

Figure 9:
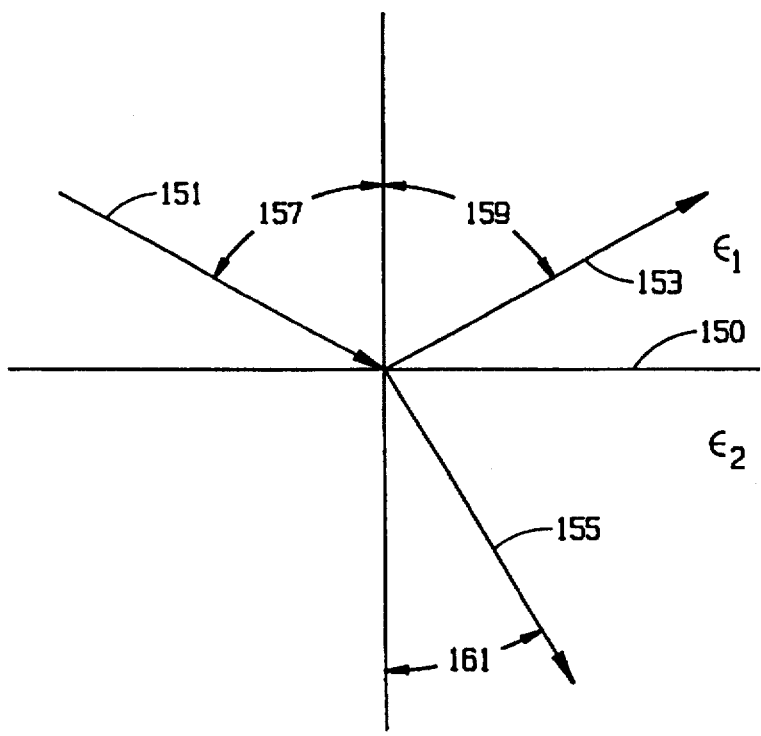
FIG. 9 shows Snell's Law effects that illustrate quasi-optical propagation from a medium with a low relative dielectric constant into a medium with a very high relative dielectric constant.

However, short focal lengths cannot be easily developed if the dielectric constant between the media that form an interface are greatly different. This would be the case if an attempt is made to propagate millimeter wave power in air and thence into the breast. As seen in FIG. 3, the dielectric constant of breast tissue is of the order of nine, and such a large value (relative to a value of one for air) causes substantial reflection of the incident power at the air-breast interface. More importantly, the apparent R/D ratio is reduced; that can lead to a radical increase in the spot size. This is best seen by referring to FIG. 9 (see Ramo (1965) p. 358 Sec. 6.13 for more complete background). Here the incident ray 151 impinges on a dielectric interface 150. This produces a reflected wave 153 and a penetrating wave 155. The angle of incidence 157 must equal the angle of reflection 159. Also, Snell's Law must be satisfied where angle 161 is the angle of the transmitted penetrating wave 155 with respect to a normal to the plane of incidence 150 and $\epsilon_1$ and $\epsilon_2$ are the dielectric constants for air and for the breast tissue, respectively:

$$[\sin 161]/[\sin 157] = [\epsilon_1/\epsilon_2]^{1/2} \qquad (7)$$

This interface reduction in the angle 161 of the transmitted penetration wave 155 will tend to increase the apparent R/D ratio (focal distance to aperture size ratio). For example, assume that a focused mm wave front with an R/D ratio of 0.5 in air impinges on a dielectric interface where the ratio of the relative dielectric constant of the second media to the first media is nine. Based on Snell's Law, the maximum value of angle 161 can be no more than about fourteen degrees. This would increase the apparent focal distance from R to about 4R and increase the spot diameter d by a factor of four.

Figure 10:
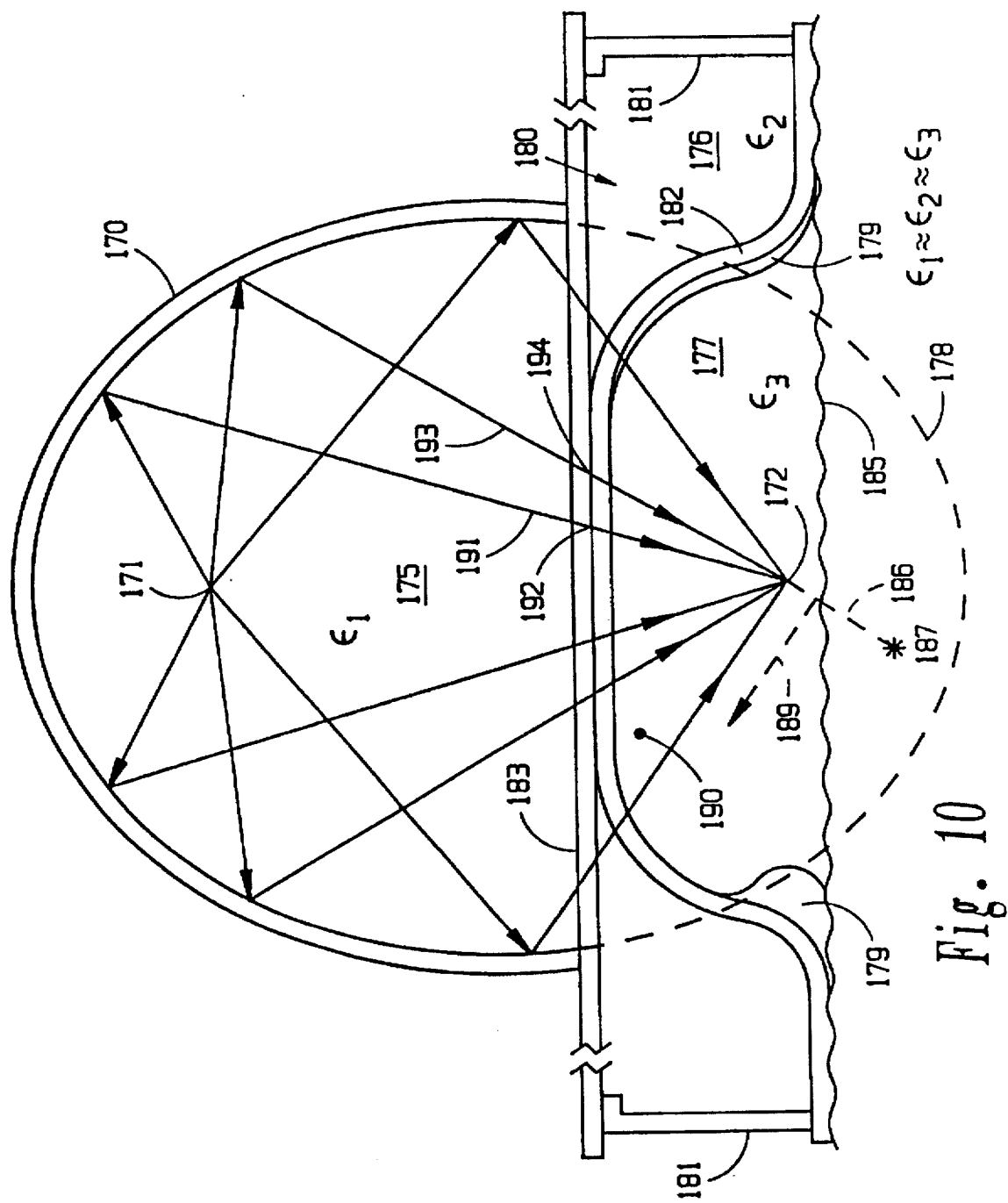
FIG. 10 is a schematic cross-sectional illustration of a large aperture illuminator in the form of an ellipsoidal reflector in combination with a boot that contains a material having relative dielectric properties similar to those for normal breast tissues.

FIG. 10 illustrates one way the defocusing and reflecting effect of the dielectric interfaces between a breast (or other tissue) and air can be mitigated. The mm wave power from a feed point 171 in a medium 175 is introduced, via an interface medium 176, into the breast 177, with the respective relative dielectric constants $\epsilon_1$, $\epsilon_2$ and $\epsilon_3$ made approximately the same. For illustrative purposes, an elliptical reflector 170 is chosen; reflector 170 has an R/D ratio of about 0.5 that would produce a spot size comparable to the wavelength, which is of the order of 6 mm. This elliptical reflector 170 and related apparatus is designed to exhibit two focal points: one at the feed point 171 and the other at a point 172 in a voxel within the breast 177. An interface boot 180 is used to contain a liquid or slurry 176 having a dielectric constant, $\epsilon_2$, that is contained by a boot wall 181, a thin, liquid-impermeable brassiere 182, and a thin, solid dielectric sheet 183 that has the same relative dielectric constant as $\epsilon_1$. For orientation purposes, the dash curve 178 represents the curve of the ellipse of reflector 170 if it were to extend into the human body.

The thin brassiere 182 is caused to fit as closely as possible to the breast 177 of the person under examination, as by withdrawing air from the voids 179. The breast is compressed into a relatively flat surface by the dielectric plate 183. This permits moving the focal point 172 by moving the elliptical reflector 170 along the surface of the dielectric plate 183 to scan the breast. The focal point 172 may be moved upwardly by increasing the thickness of the dielectric plate 183.

This arrangement assures that the mmw power that is applied to the breast is focused in the voxels of interest. Future, the millimeter wave power that is scattered from a possible tumor at the focal point 172 returns to point 171 via paths that have equal time delay, thus allowing constructive recombination of the scattered returns at the feed point 171. On the other hand, power that is not intercepted by a tumor at focal point 172 progresses on to the breast-lung interface 185 via plural paths such as the path 186. A portion 187 of the unscattered wave 186 progresses into the muscle and rib cage of the patient; another portion 189 is reflected. In order for these back-scattered or reflected muscle wall waves to add constructively at the feed point 171, the waves would have to experience the same path lengths, in terms of integral multiples of a wavelength, as for the paths of the waves scattered at the focal point 172. For most of the unscattered waves that are reflected from the breast-lung-rib cage interface, constructive addition at the feed point 171 is quite unlikely. An arrangement as shown in FIG. 10, therefore, suppresses unwanted returns or clutter from muscles and from the patient's rib cage relative to the returns that are scattered at the focal point of interest, point 172.

Other dielectric anomalies 190, such as might arise from a blood vessel, will also scatter the incident millimeter wave power. However, like the clutter returns from the muscle-rib cage, such returns will be suppressed in amplitude or even omitted, relative to the returns from the voxel containing the focal point 172. Furthermore, since many ray paths are used, any minor and random variations of the dielectric constant will tend to be averaged out.

Figure 11:
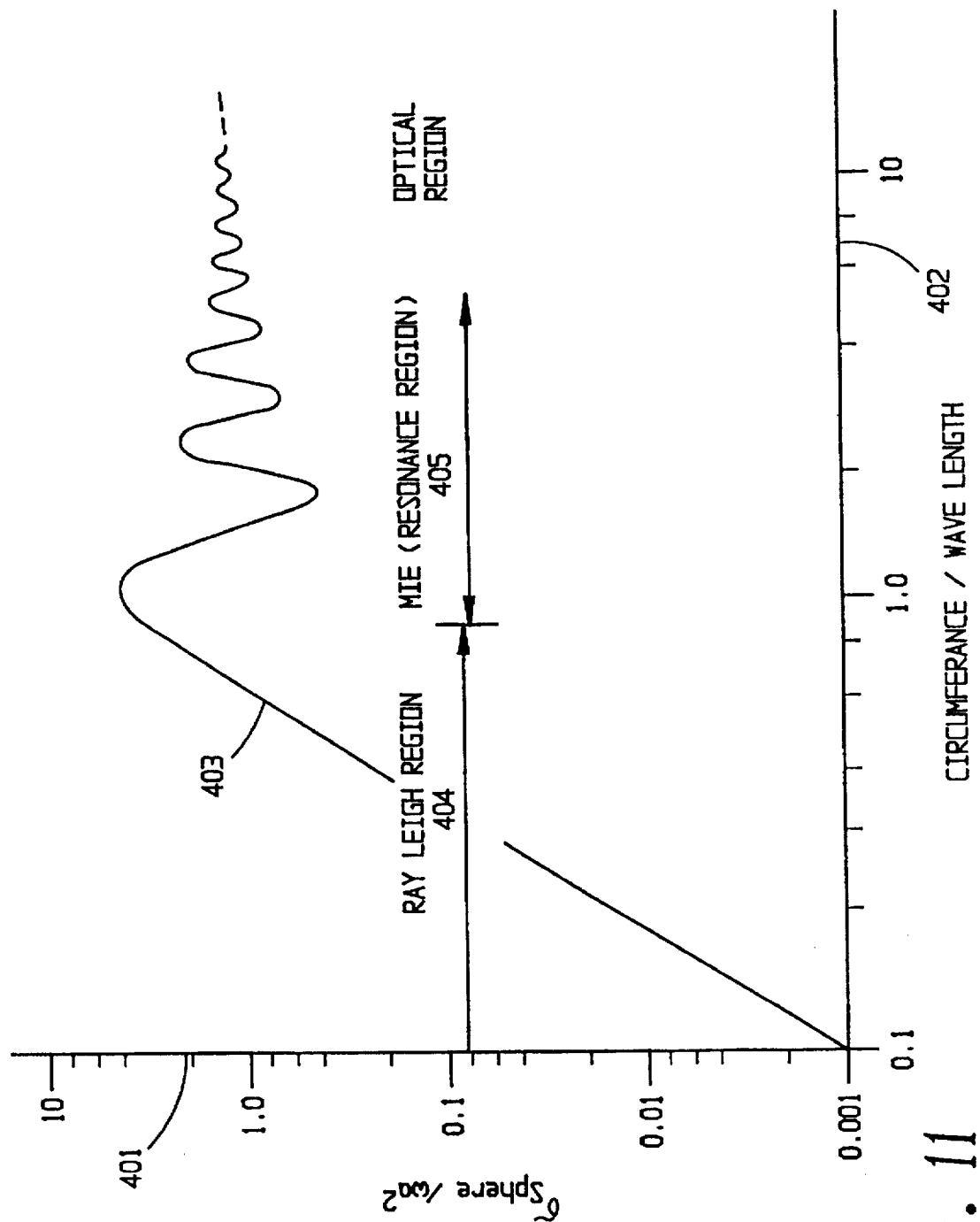
FIG. 11 is a graph that shows the backscatter cross-section of a perfectly conducting sphere normalized to the cross sectional area of the sphere as a function of the circumference-to-wavelength ratio.

Other methods of discriminating the presence of a tumor from the clutter scatter returns are possible. FIG. 11 illustrates one such phenomenon, a resonant enhancement of the scattering cross section, σ, that occurs when the circumference of a highly conductive spherical scatterer equals the wavelength in the media around the sphere. The cross-section relative to the projected area of the sphere is shown as the ordinate 401. The abscissa 402 is the ratio of the circumference to the wavelength. The curve 403 illustrates how the cross section is enhanced by the resonant scattering that takes place between the Rayliegh region 404 and the Mie (resonance) region 405. In addition, internal resonances within the tumor are possible. Despite the higher conductivity within the tumor, the material within the tumor still behaves as a lossy dielectric because of the very large value of its relative dielectric constant. Therefore, internal resonances within the very high dielectric constant tumor can be considered to occur where the internal dimensions are in the order of a one half wave length—or about 3 mm for an operating frequency of 10 GHz. Such resonances can generate a unique response, quite different from those generated from dielectric interfaces or other sources of clutter. Such resonant responses can be observed by sweeping the frequency over a wide bandwidth or exciting the breast tissues with a very short duration mmw pulse and then observing the resonant quasi-sinusoidal decay.

The foregoing description was aimed primarily at a prototype suitable for clinical evaluations. A commercial version may avoid the use of the boot and the elliptical reflector (FIG. 10). For example, arrays of 6 mm rectangular waveguides may be filled with dielectric material that has a relative dielectric constant similar to that of the breast, roughly in the order of nine to sixteen. The rectangular guide in the $TE_{01}$ mode readily propagates 10 to 15 GHz frequencies. Each of the guides would be positioned in contact with the breast, directly or through a very thin material used for one of several standard brassieres. The phase angle of the power presented to the guide-breast contact point would be identical to the phase angle of each ray path, some of which paths are shown in FIG. 10. For example, at positions 192 and 194 of FIG. 10, the phase angle of the power at each of the waveguide exits would be the same as the phase angle for each of ray paths 191 and 193 respectively. One hundred such 6 mm guides could be positioned in a 60 mm by 60 mm flat faced rectangular array to replace the egg-shaped elliptical antenna 170 shown in FIG. 10. Given a computer-aided ability to adjust the phase of the output power at each of the guides, the position of each of the guides could be made to fit the contours of many different breasts. The advantage of this approach would be to permit mass screening, but at the expense of a rather complex piece of equipment. The use of computer-controlled functions and data analysis does make such an approach feasible.

Figure 13:
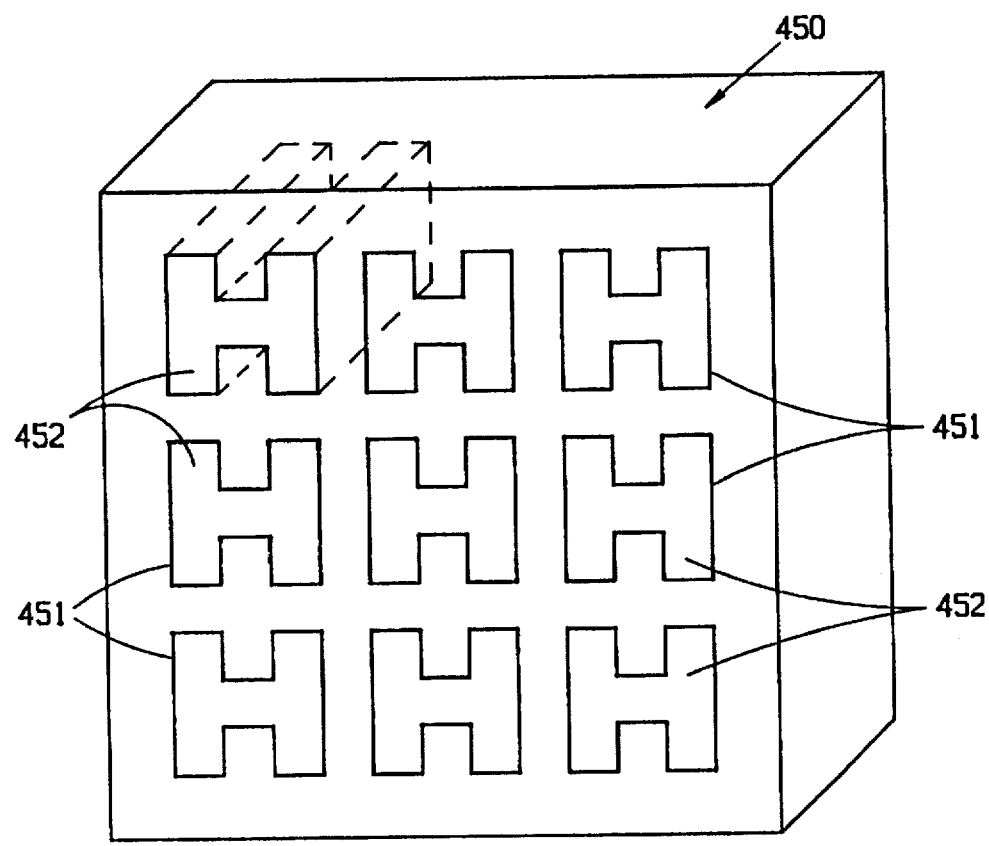
FIG. 13 illustrates an array of double ridged wave guides that can be used to replace the ellipsoidal reflector.

The foregoing can be better understood by referring to FIG. 13, which shows a nine aperture wave guide module 450. Nine double-ridged wave guides 451 are used. Each of these are filled with a dielectric material 452 that approximates the relative dielectric constant of normal breast tissue. In the case of a screening system, only four wave guide apertures might be used. The combination of modules pressed against the breast in place of the dielectric plate 183 of FIG. 10. By proper phasing of the signals to each of the wave guides, focal point can be positioned within the breast without the need for mechanical movement.

Figure 14:
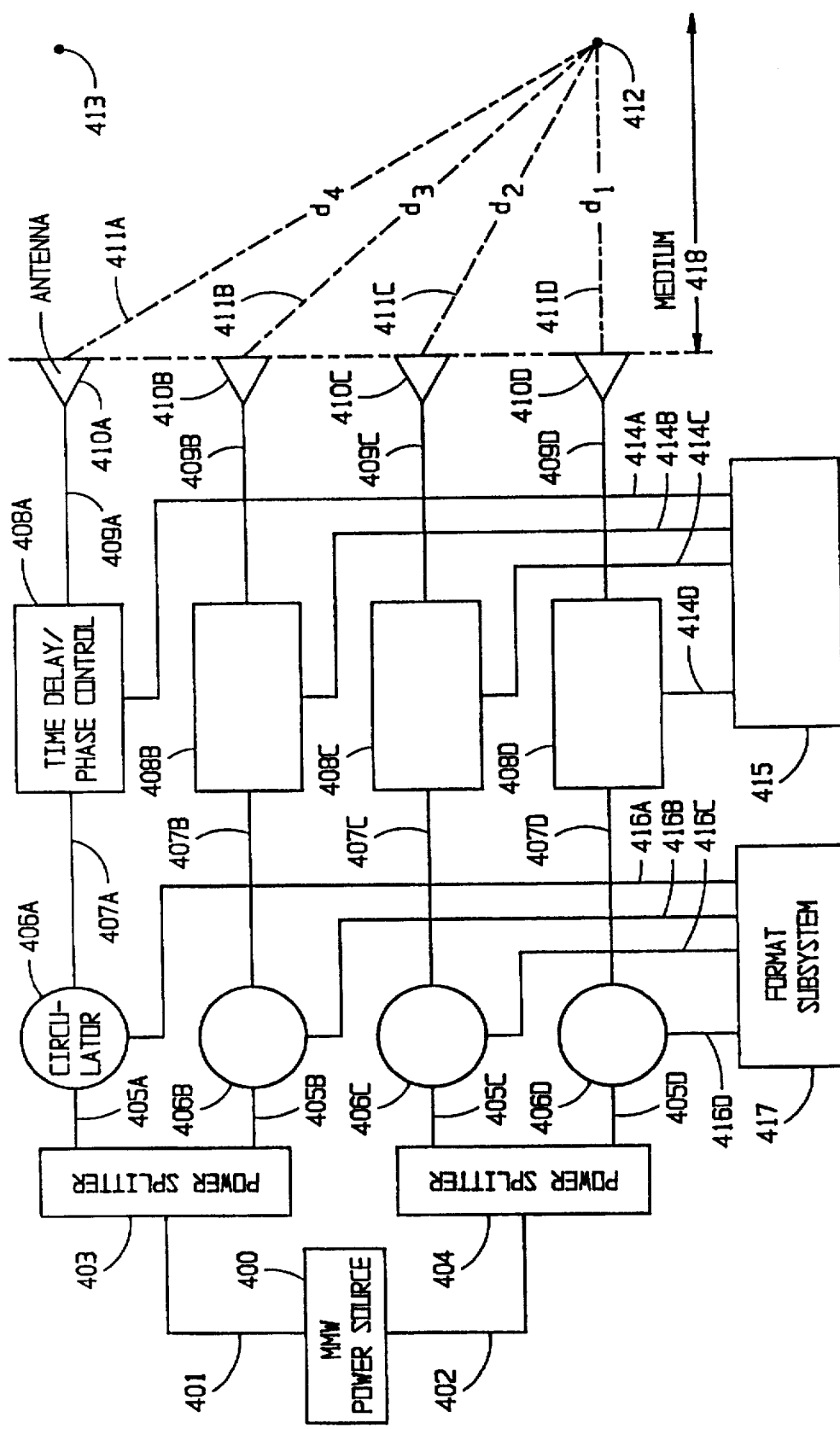
FIG. 14 presents a simplified functional block diagram on how the phased array can be controlled to position the focal point without the need for mechanical scanning.

FIG. 14 illustrates one way that the phase or timing of the signal applied to the wave guides may be controlled to position the focal point in a medium 418 which contains the aperture antennas 410A, 410B, 410C and 410D and focal points 412 and 413. A source 400 of microwave power applies equiphased power via wave guides 401 and 402 to two power splitters 403 and 404. The outputs of the splitters are applied, via wave guides 405A, 405B, 405C and 405D, to the circulators or directional couplers 406A, 406B, 406C and 406D. The forward power through these devices is transferred via the guides 407A, 407B, 407C and 407D to the variable time delay or phase control devices 408A, 408B, 408C and 408D. The return power is transferred via wave guides 416A, 416B, 416C and 416D to a subsystem 417 that collects the returns in a format suitable for additional processing by subsystem 255 of FIG. 6. The time delay in each device 408 may be controlled by changing the magnetic field bias applied to a ferrite element within each of the devices. Such bias may be supplied via the cables 414A, 414B, 414C and 414D from the time delay control subsystem 415. The outputs from wave guides 405 are controlled by the signal processing and display subsystem 255 of FIG. 6. Via wave guides 409A–409D, the time delayed or phased controlled power is supplied to the aperture antennas 410A–410D. A portion of the outputs from these apertures reaches the desired focal point 412 via pathways 411A, 411B, 411C and 411D. At point 412, the phases of the rays shown are nearly identical.

Assuming a time delay of $t_1$, $t_2$, etc. for each of the delay control elements 408 and path lengths (411) $d_1$, $d_2$, etc., then $t_1+d_1/v=d_4/v$ for constructive addition where v is the velocity of propagation in the medium 418. To meet this requirement, $t_1=(d_4-d_1)/v$. Other time delays can be calculated in the same way.

Other methods of control are possible by controlling the phase of the signals applied to each aperture instead of by the timing devices. In this case, the relative phase between the signals applied to apertures 411C and 411D can be redefined by noting the following, where ω is the radian frequency [2 πf] and $\theta_{12}$ is the phase difference between 411C and 411D, such that $\theta_{12}=\omega[t_2-t_1]$.

The confocal arrangement permits the scattered signals to return by the same pathways as the applied wave form. These signals are collected by the aperture antennas 410 and progress back through the time delay devices 408 to the circulators 406. These, in turn supply data on the scattered returns to subsystem 417.

Figure 15:
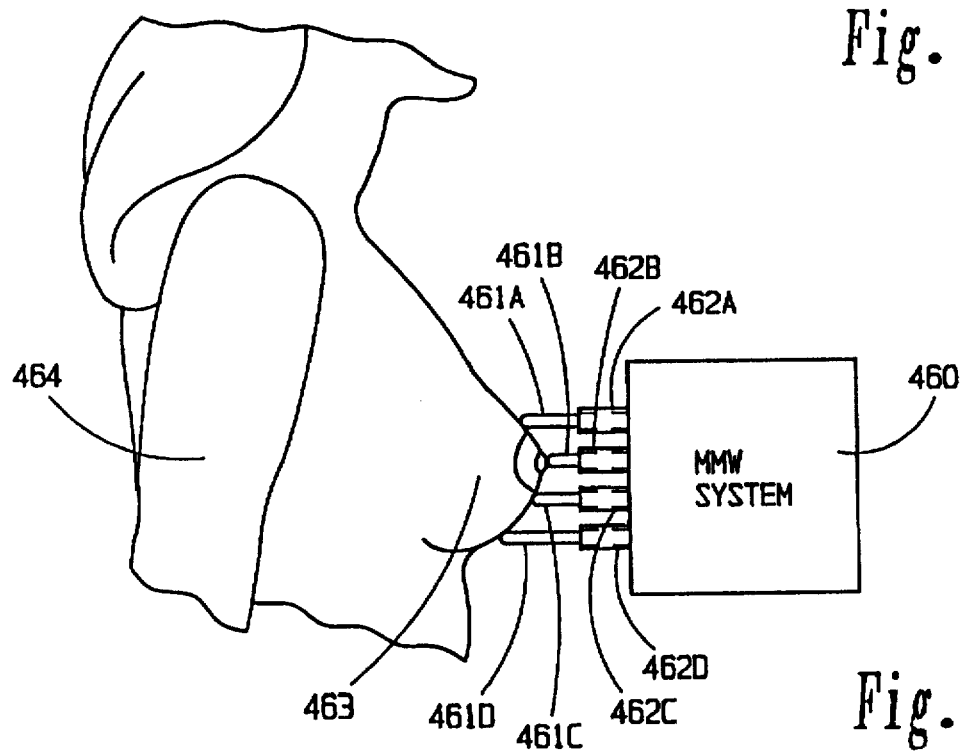
FIG. 15 shows how the a wave guide like that of FIG. 13 can be positioned directly on the breast for screening purposes.

FIG. 15 illustrates an alternate method of scanning the interior of the breast. The microwave generation and signal recovery system 460 supplies power to an array of mechanically positionable wave guides 461A, 461B, 461C and 461D. Waveguides 461 are designed to slide into guides 462 so that the distal end of guides 461 is in intimate contact with the breast 463 on the chest 464 of an examination subject. As noted before, the position of each guide can be measured and this information can be used to calculate the timing or phase data needed to position the focal point throughout the breast. This method has the advantage that an interface plate such as 183 of FIG. 10 is not needed to compress the breast 463, FIG. 15 and that better and more reproductible contact with the breast can be made.

Dielectric materials in solid form are available with relative dielectric constants that can exceed 100, that have relative low losses, and that can be machined. These materials can be used to fill the elliptical reflector or the waveguides (FIG. 10). Liquid or slurry-like dielectrics with both low losses and dielectric constants at 10 GHz in the order of ten may not be readily available. However, some liquids, such as the silicones, have dielectric constants of nearly three. Such oils could be mixed with particles of materials that have dielectric constants that exceed 30 to 50 to form a slurry exhibiting a dielectric constant of the order of nine. Conversely, acetone has a dielectric constant of 22 at ten GHz, and it could be mixed with a silicone oil to produce a dielectric constant of nine for the mixture. Other possibilities exist, including emulsions and similar techniques that allow suspensions of one liquid in another or suspensions of particles in a liquid.

The aforementioned techniques are not limited to backscatter; they can be modified or augmented to detect both side scatter and forward scatter. One forward scatter approach could use a paddle-like source antenna and a paddle-like receiving antenna. At least one of these would function similar to the antenna illustrated in FIG. 10. For example, the more pendulous portion of a breast can be placed between the paddles. This would permit examination of a breast that is 100 mm thick with a system optimized for a 50 mm penetration depth.

Figure 16:
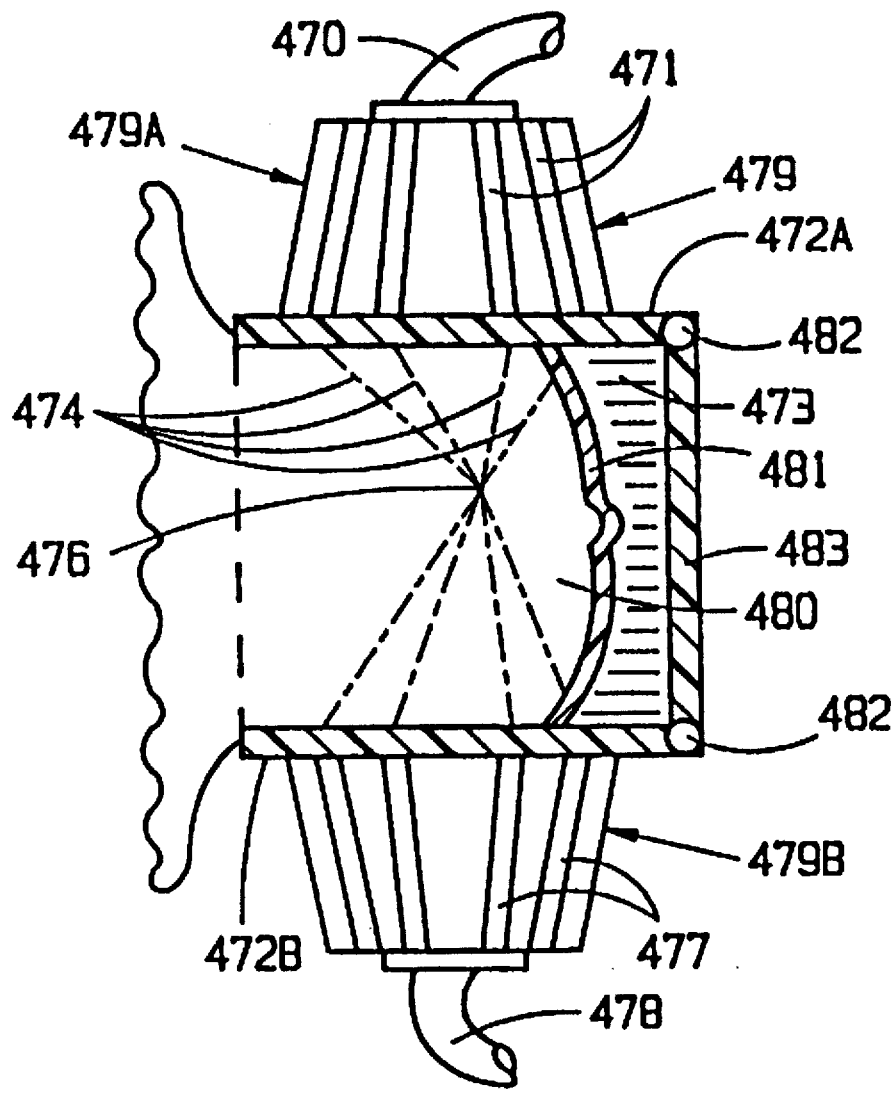
FIG. 16 illustrates how forward scattering can be sensed by a confocal arrangement wherein the focal point of the receiving array tracks the focal point of the illuminating array.

The above may be better understood by referring to FIG. 16. Here, the breast 480 is positioned within two dielectric plates 472A and 472B. A cover plate 483 and gaskets 482, together with plates 472, form a box-like structure that surrounds breast 480. The relative dielectric constant of the box wall material is similar to that of the breast. A thin plastic film 481 covers the portion of the breast that is not in contact with the box. The space between this plastic film and the breast is filled with a liquid that has the same dielectric constant as the normal breast. A cable bundle 470 supplies microwave power to a series of waveguides 471 that are in a housing 479A on plate 472A. Upon excitation, the power in these guides is timed or phased such that the ray paths 474 come to a focal point 476. The time delays in the guides 477 in the receiving assembly 479B are timed such that any scattering occuring at point 476 will add constructively. The outputs of these guides are carried to the signal processing subsystem via a cable bundle 471.

The aforementioned techniques may also be readily modified to detect Changes in the plane of polarization. For example, a square $TE_{01}$ waveguide could inject a vertically polarized wave and respond to a horizontally polarized wave. Similar arrangements could be used for either side scatter or forward scatter polarization anomaly sensing arrangements.

Another variation would be to use the illuminator and focusing arrangements described above in combination with an "active" or time domain method of separating the applied power from the scattered power. Other such active or time domain methods utilize a "chirp radar" to produce added resolution in depth and additional clutter suppression. At a center frequency of 15 GHz a chirp radar with a swept frequency bandwidth in the order of 5 GHz and with phase correction for the dielectric behavior of the breast tissue could produce range cell resolutions of the order of 10 millimeters. Alternatively, sequences of very short duration bursts of 15 to 25 GHz waveforms should also provide isolation of the applied power from the backscattered power by time gating techniques. Burst durations in the order of 100 picoseconds will provide depth discrimination of the order of 10 to 20 millimeters. This added discrimination would not only suppress the incident power, but also could suppress backscatter returns from the different dielectric interfaces, such as the muscles around the rib cage.

Active methods are of particular interest because these methods may be functional with total path losses in excess of 100 dB. Such path losses might be difficult to overcome with a passive system, since it may be difficult to reduce clutter levels below 50 to 70 dB the applied power. Since some of the clutter can be reduced by considering only the returns in just one voxel, active systems might be viable over a wider dynamic range. Also, shorter wavelengths with greater resolution can be used, since active systems can accept greater path losses, possibly as much as might be experienced by a system with an operating frequency as high as 60 GHz.

Figure 12:
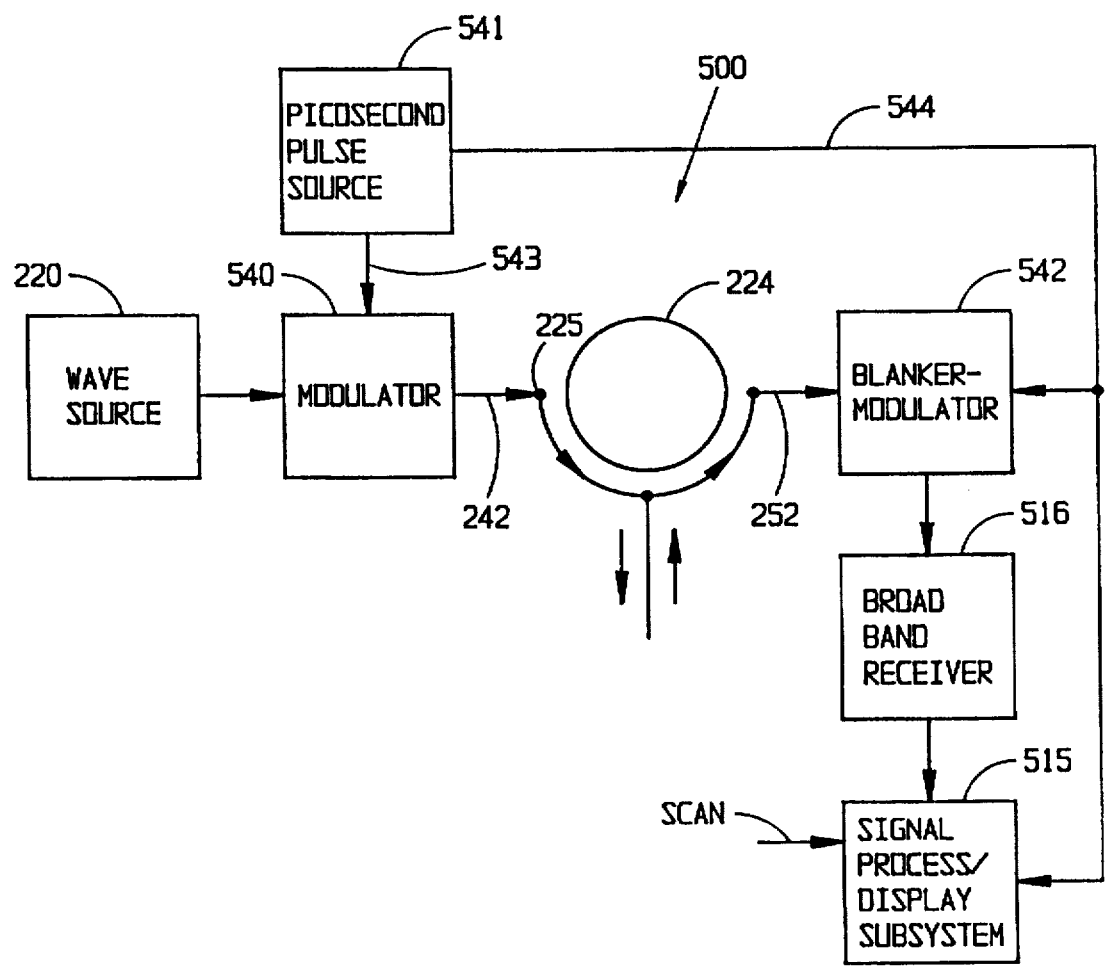
FIG. 12 presents a simplified block diagram of another detection system, according to the invention, that employs an "active" or time domain technique to help extract power scattered by a tumor from applied or impinging mmw power.

To illustrate how time domain separation can be realized in broad band pulse systems, FIG. 12 presents a further possible system 500. Many of the components are similar to those noted in FIG. 6; they are not repeated in FIG. 12. In system 500 the power and signal direction functions of the isolator of FIG. 6 have been augmented by a modulator 540 and a source 541 of 100 to 200 picosecond pulses. In some systems, the isolator 224 may be omitted. A pulse from the pulse source 541, via cable 543, gates on the modulator 540. This causes the modulator to generate a short burst of 15 GHz sine waves that is applied, via a cable 242, to the input 225 of the circulator 224. Also, the pulse source 541 supplies a timing pulse to a blanker-modulator circuit 542 and to a signal processor 515. The blanker-modulator 542 suppresses any leakage of the incident pulse through the isolator 224 from impinging on a broad-band receiver 516. The timing pulse, via the cable 544, is used by the signal processor 515 to determine the spatial position of the different scattered returns by noting the time of arrival of each of the returns. For example, the more distant returns that might arise from the patient's rib cage would be delayed the most. The combination of a pulsed sine wave source and a blanking function (often called a transmit and receive function) essentially provides a power and signal direction function that could replace the circulator 224 function as illustrated in FIG. 6.

The pico-second-duration-pulse, time-domain system described for FIG. 12 has some drawbacks that may be overcome by a stepped-frequency, synthetic-time domain method. For example, the noise level of the wide bandwidths needed to accommodate such short duration pulses can be quite high. On the other hand, the stepped-frequency method can have long well times at each frequency, thereby reducing the bandwidth and noise level for the signal processing system. While the confocal system is a powerful tool to suppress the effect of some classes of heterogeneities, it may not provide sufficient discrimination at deep penetration depths. To mitigate this problem, a time gating technique can be used to suppress scattered returns from shallow depths. Such a method may note the presence of a weakly scattering tumor at depth. If the relative dielectric constants of the intervening material are uncertain, the geometrical position of the tumor cannot be precisely determined. While this uncertainty poses a difficulty for an imaging system, it should not affect the viability of a screening system designed to detect abnormalities.

Swept frequency methods can be considered. For example, an FM Chirp radar method that has been used in weapons detection systems effectively separates desired returns from those generated by system discontinuities. A version of this would be attractive in conjunction with the confocal illumination method to separate the effects of near surface discontinuities or hetrogeneities from the returns at greater depth. Linear FM pulse compression radar (PCR) techniques might also be considered. These have been described by Jacobi (1986, reference seven hereafter) for biological imaging applications. The theoretical resolution of a PCR is given by ΔR=C/2B, where C is the is the velocity of propagation in the media, and B is bandwidth of the transmitted wave form. Assuming a mid-band frequency of 8 GHz, a 5 GHz sweep and a medium with a dielectric constant of nine, a range resolution of one cm is indicated. However, a 2.5 GHz sweep may be more readily realized and could produce an in-tissue resolution of two cm. To realize this performance, the FM sweep must be highly linear, a pulse compression filter developed for this application and the dispersion effects of the dielectric compensated.

A stepped or swept frequency input impedance Fourier inversion alternative exists. This option transforms data developed from the frequency domain measurements to the time domain via digital processing, thereby eliminating the need for a pulse compression filter. This can be implemented by using either the confocal illuminator of FIG. 10 or the phased array of FIG. 14. The output signals from the circuit shown in FIG. 7 on lines 346 and 345 can be viewed as a complex input impedance, S(jω), at a radian frequency of ω(ω=2 πf) to the illuminator. As the frequency is stepped from a low frequency to a higher frequency, the complex input impedance for each frequency is stored in a digital computer. If the frequency is swept or stepped over a band similar to that noted for the PCR system, similar spatial resolutions can be realized. Via digital processing, the complex input impedance data is converted from the frequency domain to the time domain using inverse Fourier transformation. The transformed data is then in the form of an amplitude vs. time response, similar to a radar A scope display, as if an impulse or stepped function had been applied at port 234 of the circulator 224 in FIG. 7. Initially, the returns from system discontinuities, such as from connectors and the interface with the antenna in the illuminator, will be displayed. Then, the reflections from anomalies in the breast will be displayed, the reflections from the deeper anomalies occurring at the longer times. The stepped frequency option offers the opportunity to include a standard correction at each frequency increment for a typical dispersion characteristic for normal breast tissues and could also include compensation for other factors such as path loss or system dispersion in the ferrite phase shifters. Some of the more modern network analyzers include a built-in stepped or swept frequency to time domain processing option.

The underlying mathematical basis is as follows. The general Fourier transformations are:

$$S(j\omega) = \int_{-\infty}^{+\infty} F(f) e^{-j\omega t} dt$$

$$F(f) = \frac{1}{2\pi} \int_{-\infty}^{+\infty} S(j\omega) e^{j\omega t} d\omega$$

Where F(f) is the impulse or step response
S(jω) is the Fourier transformation of F(f)
ω=2 π f, is time.

Throughout the foregoing specification and in the appended claims the terms millimeter waves, or mm waves or mmw have been used to generically represent the wavelengths of the electromagnetic waves that propagate in the human breast tissue. Since the relative dielectric constant of the breast is in the order of 9 to 12, the free-space wave length will be reduced by a factor of three or more. Thus, the in-tissue wavelengths over a frequency range of 3 to 60 GHz will range from about 30 mm to 1 mm.

As opposed to certain microwave hypothermia cancer treatment technology, none of the technology presented here is intended to heat significantly any portion of the breast. This requirement limits the power deposition density onto the surface of the breast to less than 10 milliwatts/cm$^2$ and the volumetric heating rate in any portion of the breast to less than 0.8 milliwatts per gram of tissue as averaged over a time period of a few minutes. To further assure minimal thermal effects, the input power is to be turned off if the scanning system falters for any reason.

Other usages are as follows: The term impedance refers to the ratio of the voltage to the current or of the electric field to the magnetic field at a specified location. This term impedance is qualified as "electrical" or "wave" respectively, depending on whether voltages and currents or electromagnetic fields are concerned. The term wave guide is used in the generic sense and includes both cables and higher mode wave guides with just a single transverse field. The terms effective aperture and effective focal point are used in the generic sense wherein apertures and focal points can be created physically or synthetically (such as often used in synthetic aperture radar).

The effective focal point is not really a point but rather is defined here as a region where the illuminating energy is most concentrated in the breast. The effective focal point is further defined as the region or volume where this energy concentration occurs as affected by the heterogeneity of dielectric characteristics of the normal breast tissues, the in-tissue wavelength, the size and distance of the illuminating globular aperture or the geometry and number of apertures used in a phased array. The focal point positioning may be either mechanical or electronic as in the case of a phased array.

The terms "detect" or "detection" are also used in the generic sense, and may mean simply indicating the presence of a tumor or more broadly providing data that permits imaging the location, size and geometry of the tumor. Detecting, identifying, imaging or locating a tumor also means noting the presence of an abnormality. The terms "power and signal director" or "input power and signal separation" are also used in a generic sense. Both passive and active techniques not only enhance detection by suppressing the direct effects of impinging power waves, but also can reduce false signals or clutter. Such are introduced by imperfect matches between impedances or by non-tumor scattering sources, such as the breast/lung interface.

The following references are of utility in understanding the foregoing specification:

Burdette, E. C., et. al.(1980): In vivo measurement techniques for determining dielectric properties at VHF through microwave frequencies, IEEE Trans. on MTT, Vol MTT-28, No. 4 April, pp 414–427

Burdette, E. C., et. al. (1986): In situ permittivity at microwave frequencies: perspective, techniques, results, medical applications of microwave imaging, Medical Applications of Microwave Imaging, Larsen, L. E. and J. H. Jacobi, IEEE press pp 13–40

Chaudhary, S. S., et. al. (1984): Dielectric properties of normal and malignant human breast tissues at radiowave and microwave frequencies, Indian Jr. of Biochemistry and biophysiscs, Vol. 21, Feb pp76–79

Edrich, J., et. al. (1976): Complex permittivity and penetration depth of muscle and fat tissues between 40 and 90 GHz, (1976) IEEE Trans. MTT, vol. MTT-24, May pp273–275.

Johnson, E. C., et. al. (1972): Nonionizing electromagnetic wave effects in biological materials and systems, Proc. of the IEEE, Vol. 60, No. 6, June pp 694–695.

Kay, A. F. (1966): Millimeter wave antennas, Proc. of the IEEE, Vol. 54, No. 4, pp 641–647

Larsen, E. L. and J. H. Jacobi, Eds. (1986): Medical Applications of Microwave Imaging, IEEE press. Institute of Electrical and Electronic Engineers, New York, pp. 138–147

Ramo, S., et. al. (1965): Fields and Waves in Communication Electronics, John Wiley and Sons, New York Rogers, J. A., et. al. (1983): The dielectric properties of normal and tumor mouse tissue between 50 MHz and 10 GHz, British Jr. of Radiology, vol. 56, May, pp 335–338.

Smith, W. J., (1966): Modern Optical Engineering, Mc Graw-Hill, New York, N.Y.

I claim:

1. A non-invasive system utilizing non-ionizing electromagnetic millimeter waves of minimal thermal heating capacity for detection of a tumor in a breast, comprising:

a generator for generating a non-ionizing high-frequency electromagnetic input wave;

illumination means for creating an effectively focussed non-ionizing electromagnetic beam from the input wave and directing said beam to impinge upon an effective focal point at a predetermined position within a breast;

wave impedance matching means, in the illumination means, matching the impedance of the illumination means to the wave impedance of normal breast tissue;

a wave guide for applying the input wave from the generator to the breast through the illumination means;

focal point shifting means, connected to the illumination means, for shifting the effective focal point across the breast in a predetermined pattern to scan selected incremental volumes within the breast;

at least one scattered wave collector positioned to intercept scattered waves from the incremental volumes within the breast and develop a return signal representative of the scattered waves from within the breast;

and a receiver, including a detector, connected to the scattered wave collector, for detecting anomalies in the return signal to identify a tumor and its location in the breast.

2. A non-invasive system for detection of a tumor in a breast according to claim 1 and further comprising:

separator means, connected to the scattered wave collector, for separating the scattered wave signals from the input wave in developing the return signal.

3. A non-invasive system for detection of a tumor in a breast according to claim 2 in which the separator means includes a circulator.

4. A non-invasive system for detection of a tumor in a breast according to claim 2 in which the separator means includes polarization-responsive means for separating the input wave from the return signal based on polarization of the return signal.

5. A non-invasive system for detection of a tumor in a breast according to claim 2 in which:

the separator means includes a pulse source of repetitive pulse signals; and the system further comprises display means, connected to the pulse source of the separator means and to the receiver, for displaying the returns as a function of time;

the rise time for each pulse signal being no greater than 300 pico-seconds.

6. A non-invasive system for detection of a tumor in a breast according to claim 2 in which the pulse source is a part of a frequency-modulated pulse compression system that employs a frequency bandwidth of at least two gigahertz.

7. A non-invasive system for detection of a tumor in a breast according to claim 2 and further comprising compensation means for compensating for change in the dielectric constant of the breast as a function of frequency.

8. A non-invasive system for detection of a tumor in a breast, according to claim 2, in which a synthetic time-domain response is developed from the Fourier inversion of the complex input impedance data as the frequency of the illumination signal is progressively changed over a bandwidth of at least two gigahertz.

9. A non-invasive system for the detection of a tumor, according to claim 8, and further comprising means to compensate for the changes in the equipment behavior as a function of frequency.

10. A non-invasive system for the detection of a tumor, according to claim 8, and further comprising means to compensate for the path loss attenuation as the illuminating signal progresses into the breast.

11. A non-invasive system for detection of a tumor in a breast according to claim 1, in which:

the reflection receiver is a part of the illumination means;

and further comprising separator means, connected to the scattered wave collector, for separating the scattered wave signals from the input wave in developing the return signal.

12. A non-invasive system for detection of a tumor in a breast according to claim 1 in which:

the illumination means comprises a globular antenna filled with a first dielectric medium;

the illumination means further comprises a connecting device, connecting the antenna to the breast, filled with a second dielectric medium; and the dielectric constants of the breast, the first dielectric medium, and the second dielectric medium are all approximately equal to each other.

13. A non-invasive system for detection of a tumor in a breast according to claim 12 in which the globular antenna is of truncated ellipsoidal configuration and functions as a part of the transmitter and a part of the collector.

14. A non-invasive system for detection of a tumor in a breast, according to claim 12, in which the dielectric constants are in a range of four to twenty.

15. A non-invasive system for detection of a tumor in a breast according to claim 1 in which the focal point shifting means includes a mechanical scanner to change the location of the illuminator means relative to the breast.

16. A non-invasive system for detection of a tumor in a breast according to claim 15 and further comprising:

focal point indication means, connected to the mechanical scanner; and imaging means, connected to the receiver and to the focal point indication means, for displaying an image of the breast including a representation of any tumor therein.

17. A non-invasive system for detection of a tumor in a breast according to claim 1 in which the connection from the generator to the receiver includes a phase shift circuit for shifting the input wave, as applied to one of the detectors, by an odd multiple of 90° relative to the input wave as supplied to the other detector.

18. A non-invasive system for detection of a tumor in a breast according to claim 17 in which each of the detectors is a hybrid tee.

19. A non-invasive system for detection of a tumor in a breast according to claim 1 in which the distance from the effective focal point to the effective aperture of the illuminator is no greater than four times the diameter of the effective aperture.

20. A non-invasive system for detection of a tumor in a breast, according to claim 1, comprising at least two scattered wave collectors, disposed on opposite sides of the breast.

21. A non-invasive system for detection of a tumor in a breast, according to claim 1, in which the receiver includes a directional coupler.

22. An illumination means for a non-invasive system for the detection of a tumor in a breast according to claim 1 comprising:

an array of a plurality of independently excitable wave guides, each having an excitation end and an open end;

means to note the position of the contact point of each illuminator wave guide between the open end of the wave guide and the surface of the breast, with no more than a minimum space between the wave guide and the breast;

means to control the phase angle of the input wave of each illuminator wave guide at its contact point in accordance with the position of the contact point; and means to change the phase angle of the input wave of each illuminator wave guide at its contact point such that the individual waves that propagate from each of the illuminator wave guides into the breast add constructively at an effective focal point within a predetermined incremental volume within the breast.

23. An illumination means for a non-invasive system for detection of a breast tumor according to claim 22 and further comprising means to move the array of wave guides and the interface mechanically to scan the breast.

24. An illumination means according to claim 22 and further comprising:

means to controllably and independently position the open ends of the illuminator wave guides into predetermined positions on the surface of the breast.

25. An illumination means according to claim 22 in which the illuminator wave guides are each filled with materials that have dielectric characteristics similar to that for the human breast.

26. A scattered wave collector for a non-invasive system for the detection of a tumor in the breast, including an illumination means according to claim 22, that further includes a scattered wave collector positioned to intercept waves scattered from the effective focal point, comprising:

an array of a plurality of collector wave guides, each having an open end;

means to note the position of the contact point of the open end of each collector wave guide and the surface of the breast; and means to control the phase angle of each of the waves collected by each collector wave guide such that the collected scattered waves that propagate from the effective focal point in the breast to each of the collector wave guides on the surface of the breast are constructively combined.

27. A wave collection means for a non-invasive system for the detection of a tumor, according to claim 26, in which the illuminator wave guides are also the collector wave guides.

* * * * *